(12) United States Patent
Wan et al.

(10) Patent No.: US 11,786,471 B2
(45) Date of Patent: *Oct. 17, 2023

(54) COMPLEX DISINTEGRANT SYSTEM FOR ORAL SOLID PREPARATION AND ORAL SOLID PREPARATION COMPRISING SAID COMPLEX DISINTEGRANT SYSTEM

(71) Applicant: WUHAN LL SCIENCE AND TECHNOLOGY DEVELOPMENT CO., LTD., Hubei (CN)

(72) Inventors: Yaowen Wan, Hubei (CN); Yongkai Chen, Hubei (CN); Xian Zeng, Hubei (CN); Chaodong Wang, Hubei (CN); Wei Feng, Hubei (CN)

(73) Assignee: WUHAN LL SCIENCE AND TECHNOLOGY DEVELOPMENT CO. LTD., Hubei (CN)

( * ) Notice: Subject to any disclaimer, the term of this patent is extended or adjusted under 35 U.S.C. 154(b) by 598 days.

This patent is subject to a terminal disclaimer.

(21) Appl. No.: 16/312,948

(22) PCT Filed: Jun. 27, 2017

(86) PCT No.: PCT/CN2017/090374
§ 371 (c)(1),
(2) Date: Dec. 21, 2018

(87) PCT Pub. No.: WO2018/010543
PCT Pub. Date: Jan. 18, 2018

(65) Prior Publication Data
US 2019/0328673 A1 Oct. 31, 2019

(30) Foreign Application Priority Data
Jul. 11, 2016 (CN) .......................... 201610539612.7

(51) Int. Cl.
*A61K 9/20* (2006.01)
*A61P 9/12* (2006.01)
*A61K 31/4245* (2006.01)
*A61K 31/497* (2006.01)

(52) U.S. Cl.
CPC .............. *A61K 9/2072* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 31/4245* (2013.01); *A61K 31/497* (2013.01); *A61P 9/12* (2018.01)

(58) Field of Classification Search
CPC .............. A61K 31/4245; A61K 31/497; A61K 9/2072; A61K 9/12; A61K 9/20; A61K 9/2009; A61K 9/2013; A61K 9/2018; A61K 9/2027; A61K 9/2054; A61K 9/2059

See application file for complete search history.

(56) References Cited

U.S. PATENT DOCUMENTS

| | | | |
|---|---|---|---|
| 8,632,819 B2 * | 1/2014 | Thoorens | A61K 9/2009 424/499 |
| 9,708,306 B2 * | 7/2017 | Ge | A61P 5/50 |
| 11,008,311 B2 * | 5/2021 | Lei | C07D 413/14 |
| 11,013,736 B2 * | 5/2021 | Liang | A61P 9/12 |

FOREIGN PATENT DOCUMENTS

| | | | | |
|---|---|---|---|---|
| CN | 105153141 A | | 12/2015 | |
| WO | WO2014/102628 | * | 7/2014 | ......... A61K 31/4245 |

OTHER PUBLICATIONS

Hong, Qiubing et al., "Preparation for Zinc Gluconate Effervescent Tablets and its Quality Control", Clinical Journal of Medical Officer, vol. 41, No. 2, Feb. 15, 2013.

* cited by examiner

*Primary Examiner* — Alicia L Otton
(74) *Attorney, Agent, or Firm* — NKL Law; Allen Xue

(57) ABSTRACT

A complex disintegrant composition for oral solid preparation, comprising a disintegrant and a disintegrating aid, the disintegrant being a hygroscopic expansion type disintegrant, the disintegrating aid being a soluble small molecule substance or a gas-producing type salt. An oral solid preparation, comprising an active ingredient, said complex disintegrant composition, an excipient and a lubricant.

13 Claims, 2 Drawing Sheets

COMPLEX DISINTEGRANT SYSTEM FOR ORAL SOLID PREPARATION AND ORAL SOLID PREPARATION COMPRISING SAID COMPLEX DISINTEGRANT SYSTEM

TECHNICAL FIELD

Embodiments of the present disclosure relate to the field of pharmaceutical preparations, and specifically relate to a complex disintegrant system for oral solid preparations and an oral solid preparation comprising the complex disintegrant system.

BACKGROUND

In general, the rate of absorption of an oral solid preparation depends on the rate at which the active substance (active ingredient) is dissolved (released) from the solid preparation, and the rate of dissolution (release) of the active ingredient often depends on the rate of disintegration of the solid preparation. In conclusion, it can be considered in general that the rate of disintegration of an oral solid preparation is a determining step of the absorption rate of the active ingredient by the body. Due to good water absorption and swelling properties of most disintegrants, adding a disintegrant to an oral solid preparation facilitates eliminating or destroying the binding force caused by an adhesive or high compression, thus promoting dissolution and absorption of the active ingredient, while rapidly fragmented into fine particulate matter in the dissolution medium, and thereby exerting a therapeutic effect. The disintegration mechanism of the disintegrant is mainly based on capillary action and swelling property. Specifically, the disintegrant forms capillary channels which are easy to wet in an oral solid preparation. Accordingly, when a solid preparation is placed in a dissolution medium, the dissolution medium rapidly enters the solid preparation through the capillaries, making the entire solid preparation wetted, so that the disintegration of the oral solid formulation undergoes a wetting, siphoning, swelling and breaking process.

Commonly used disintegrants are dry starch, sodium carboxymethyl starch, low-substituted hydroxypropyl cellulose, crospovidone, croscarmellose sodium (CMC-Na), and the like, which promote the disintegration of a solid preparation mainly through effects of capillary action and swelling property. However, there exist some active substances with high hygroscopicity, which become sticky after moisture absorption and are thereby unable to be effectively disintegrated by any conventional disintegrant, resulting in poor dissolution and release properties of them.

Chinese Patent Application (Publication No. CN103709154A) discloses a compound of the formula (I) as below for the first time:

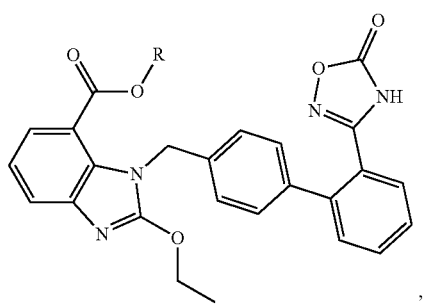

(I)

The above compound is a sartan drug which is coupled with ligustrazine and is a prodrug of angiotensin II receptor antagonist azisartan (TAK-536). The compound releases hydroxyprosin or NO in vivo, which makes an effective synergistic action with azilsartan, accordingly enhancing its antihypertensive effect as well as contributing to reduction of heart rate and adverse effect, and further bringing desired protective effect on the heart and kidney of patients. A potassium salt of compound (I), represented by the compound of formula (II) as below, has been discovered by the inventors in further studies, which has better solubility, higher bioavailability, more potent and longer-lasting antihypertensive effect, more obvious and sustainable effect of lowering heart rate, higher safety, as well as desired protective effect on the heart and kidney function of patients, and can be used for preventing and/or treating hypertension, chronic heart failure, diabetic nephropathy, and the like.

During the process of preparing the compound of formula (I) and formula (II) into an oral solid preparation, all kinds of conventional disintegrants are unable to work, resulting in poor dissolution release properties of the active ingredient. It has been found that most of these compounds have high hygroscopicity and become sticky after moisture absorption, which makes conventional disintegrants ineffectual in disintegration, resulting in poor dissolution and release properties of the active ingredients by further research of the inventors.

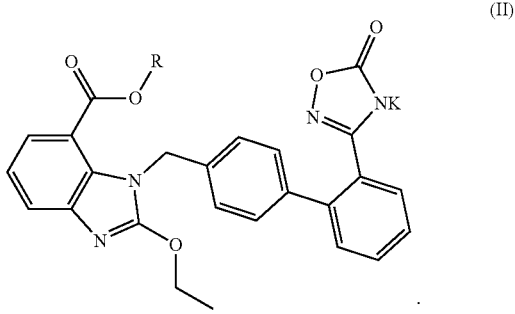

(II)

SUMMARY

A complex disintegrant system for oral solid preparations is provided in an embodiment of the present disclosure, which can rapidly disintegrate the oral solid preparation, increase the dissolution rate thereof, thereby improving its bioavailability, and particularly solve the problem referring to ineffectiveness of conventional disintegrants to disintegrate active substances (active ingredients) which have high hygroscopicity and become sticky after moisture absorption effectively.

Conventional disintegrants promote the disintegration of a solid preparation mainly relying on the effect of capillary action which introduces water into the interior of the solid preparation and swelling property of disintegrants due to water absorption which eliminates the binding force caused by an adhesive or high compression. If active substances (active ingredients) have high hygroscopicity and therefore become sticky after moisture absorption, oral solid preparations comprising the above active substances and conventional disintegrants become difficult to disintegrate. For example, the above solid preparation is unable to disintegrate and release drug under simulated gastric acid pH conditions. This is probably because the active substances (active ingredients), which have high hygroscopicity, competing with conventional disintegrants to absorb moisture, and become sticky after water absorption, interfere with swelling of the disintegrant and block the water access channels, thus making the conventional disintegrants difficult to exert their disintegration performance.

In an embodiment of the present disclosure, a complex disintegrant system for oral solid preparations, comprising a disintegrant and a disintegrant assistant is provided. Preferably, the complex disintegrant system for oral solid preparations consists of a disintegrant and a disintegrant assistant.

In an embodiment of the present disclosure, the disintegrant used herein is a hygroscopic swelling type disintegrant. Preferably, the hygroscopic swelling type disintegrant comprises at least one selected from the group consisting of: dry starch, croscarmellose sodium, sodium carboxymethylcellulose, calcium carboxymethylcellulose, sodium carboxymethyl starch, methylcellulose, low substituted hydroxylpropyl cellulose, crospovidone, chitosan and microcrystalline cellulose.

In an embodiment of the present disclosure, the disintegrant assistant used herein is a soluble small molecule or a gas generating type salt. Preferably, the gas generating salt comprises at least one selected from the group consisting of: carbonate and hydrogencarbonate. More preferably, the gas generating salt comprises at least one selected from the group consisting of: sodium carbonate, calcium carbonate, potassium carbonate, calcium magnesium carbonate, zinc carbonate, magnesium carbonate, ammonium carbonate, sodium glycine carbonate, sodium sesquicarbonate, sodium hydrogencarbonate, calcium hydrogencarbonate, potassium hydrogencarbonate and ammonium hydrogencarbonate.

Preferably, the soluble small molecule comprises at least one selected from the group consisting of: sodium chloride, glucose, fructose and xylitol; more preferably, the soluble small molecule comprises at least one selected from the group consisting of: sodium chloride and glucose.

In an embodiment of the present disclosure, preferably, a weight ratio of the disintegrant to the disintegrant assistant is from 10:1 to 1:10; more preferably, from 8:1 to 1:8; most preferably, from 5:1 to 1:5.

In an embodiment of the present disclosure, the disintegrant assistant is an assistant agent capable of facilitating the disintegration of an active substance (active ingredient) which is highly hygroscopic and becomes sticky after moisture absorption. It is found that this kind of active substance (active ingredient) which cannot be effectively disintegrated using any conventional disintegrant can be disintegrated by addition of the soluble small molecule or the gas generating type salt, which is accordingly defined as a disintegrant assistant herein.

In an embodiment of the present disclosure, the complex disintegrant system may also be referred to as a complex disintegrant composition or a complex disintegrant. The complex disintegrant system of embodiments of the present invention, when used to formulated an oral solid preparation, due to the introduction of dissolution medium and rapidly dissolution of the soluble small molecule as a disintegrant assistant, not only forms capillary channels inside the oral solid preparation, but also brings internal and external osmotic pressure difference of the oral solid preparation, which accordingly leads to introduction of dissolution medium into the interior of the oral solid preparation and promotes the water-swelling disintegrant to cause disintegration of the solid preparation. When the gas generating type salt is selected as a disintegrant assistant, it releases gas while contacting with the dissolution medium, thereby forming a space for introducing water, which on one hand promotes water swelling of the disintegrant to cause disintegration, and on the other hand generates gas pressure inside the oral solid preparation to promote disintegration of the solid preparation. The dissolution medium used herein refers to gastric juice, intestinal fluid, simulated gastric juice, or simulated intestinal fluid.

Therefore, the complex disintegrant system provided by embodiments of the present invention is particularly suitable for an active substance (active ingredient) which cannot be effectively disintegrated by any conventional disintegrant, for example, an active substance (active ingredient) which is highly hygroscopic and becomes sticky after moisture absorption, including but not limited to a compound represented by the following formula (I) or formula (II):

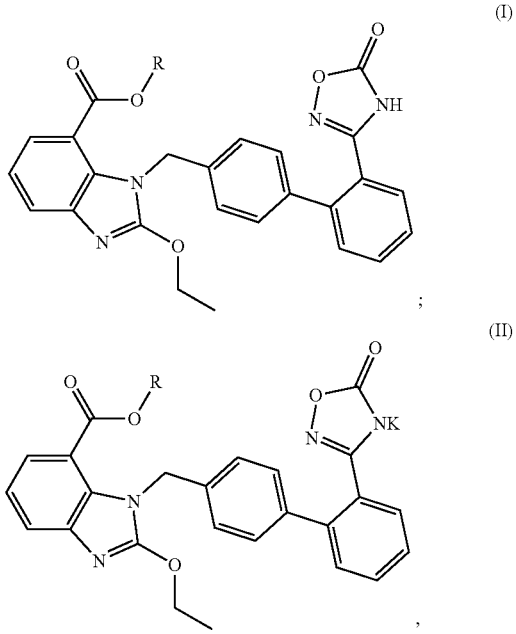

wherein in formula (I) and formula (II), R represents

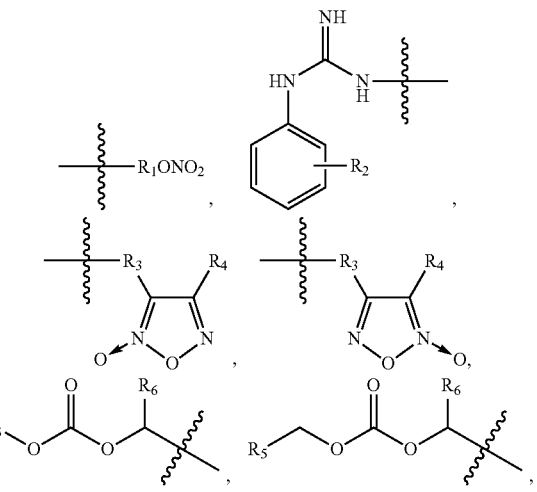

-continued

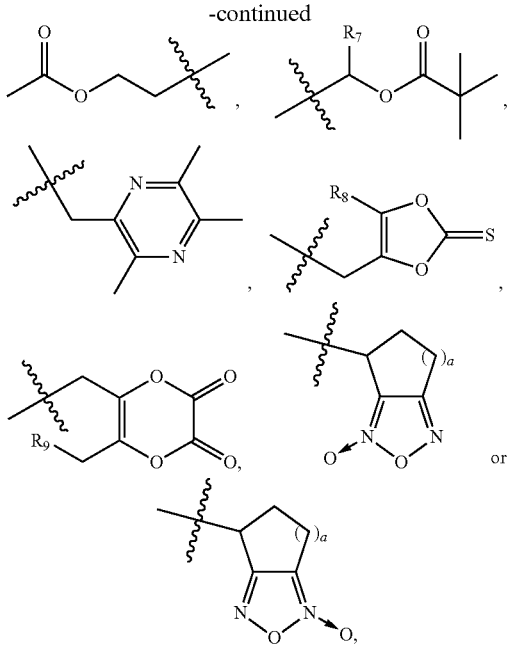

wherein, a=0, 1, 2, 3, 4, 5 or 6;

wherein, $R_1$ represents $C_2$-$C_8$ alkyl, $C_2$-$C_8$ alkene, $C_2$-$C_8$ alkyne,

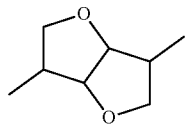

$(CH_2)_nO(CH_2)_m$,

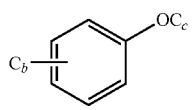

aryl group (such as phenyl), substituted aryl group (such as substituted phenyl group), heteroaryl group or substituted heteroaryl group, wherein, $C_b$, $C_c$ in

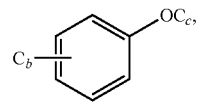

independently represent H or alkyl, wherein, b, c represent the number of carbon atoms, each independently selected from 0, 1, 2, 3, 4, 5 or 6;

wherein n, m in $(CH_2)_nO(CH_2)_m$ are each independently selected from 1, 2, 3, 4, 5 or 6;

wherein $R_2$ represents hydrogen, halogen, trifluoromethyl, $C_1$-$C_8$ alkoxy, $C_1$-$C_8$ alkyl, nitro, sulfonamide, amino or nitrile;

wherein $R_3$ represents null, $C_1$-$C_8$ alkyl, $C_1$-$C_8$ alkoxy, $C_2$-$C_8$ alkeneoxy, $C_2$-$C_8$ alkyneoxy, $(C_1$-$C_6)O(C_1$-$C_6)$,

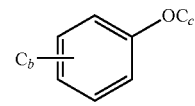

aryl group (such as phenyl), substituted aryl group (such as substituted phenyl group), heteroaryl group or substituted heteroaryl group, wherein, $C_b$, $C_c$ in

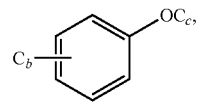

independently represent H or alkyl, wherein, b, c represent the number of carbon atoms, each independently selected from 0, 1, 2, 3, 4, 5 or 6;

wherein $R_4$ represents aryl group (such as phenyl), substituted aryl group (such as substituted phenyl), arylsulfonyl group (such as phenylsulfonyl), 5-6 membered heteroaryl group, 5-6 membered substituted heteroaryl group, nitrile, trifluoromethyl, $C_1$-$C_8$ alkoxy, $C_1$-$C_8$ nitrate, $C_1$-$C_8$ alkyl, —$CH_2ONO_2$;

wherein $R_5$ represents aryl group (such as phenyl), substituted aryl group (such as substituted phenyl group), 5-6 membered heteroaryl group, 5-6 membered substituted heteroaryl group, nitrile, trifluoromethyl, $C_1$-$C_8$ alkoxy, $C_1$-$C_8$ nitrate, $C_1$-$C_8$ alkyl, $C_1$-$C_8$ alkene, $C_1$-$C_8$ alkyne,

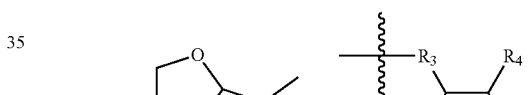

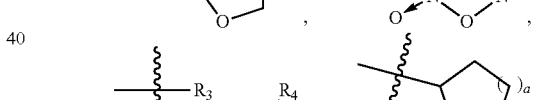

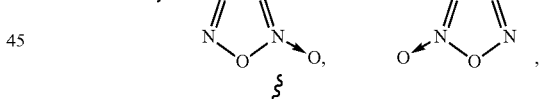

or $(CH_2)_nO(CH_2)_m$, wherein $R_3$, $R_4$, a, m, n are as defined above;

wherein $R_6$ and $R_7$ represent hydrogen, $C_1$-$C_8$ alkoxy or $C_1$-$C_8$ alkyl;

wherein $R_8$ and $R_9$ represent hydrogen, $C_1$-$C_8$ alkoxy, $C_1$-$C_8$ nitrate or $C_1$-$C_8$ alkyl;

wherein the aryl group refers to an aryl group with a 6-20 membered monocyclic or a fused ring such as phenyl or naphthyl;

wherein the substituted aryl group refers to an aryl group substituted by one or more selected from the group consisting of hydroxyl, $C_1$-$C_6$ alkyl, $C_1$-$C_6$ alkoxy, halogen, nitro, amino, nitrile, trifluoromethyl, oxo, —CH=CHCO$_2$R$_{11}$, wherein each substituent may be the same or different, wherein $R_{11}$ represents hydrogen or $C_1$-$C_6$ alkyl;

wherein the heteroaryl group refers to a 5-20 membered aryl group (preferably a 5 to 7 membered aryl group) having 1 to 4 hetero atoms, each of which is independently selected from O, S or N; preferably, the heteroaryl group is selected from the group consisting of furanyl, thienyl, pyrrolyl, pyridyl, pyrimidinyl, thiazolyl, thiadiazolyl, quinolinyl, indolyl and the like;

wherein the substituted heteroaryl group is a heteroaryl group substituted by one or more selected from the group consisting of $C_1$-$C_6$ alkyl, $C_1$-$C_6$ alkoxy, halogen, wherein each substituent may be same or different.

In a preferred embodiment, the compound of formula (I) has one of the structures shown below:

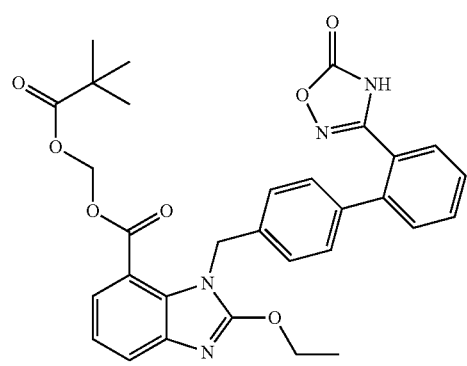
QR01005

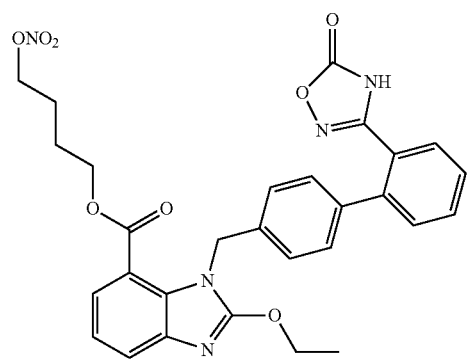
QR01008

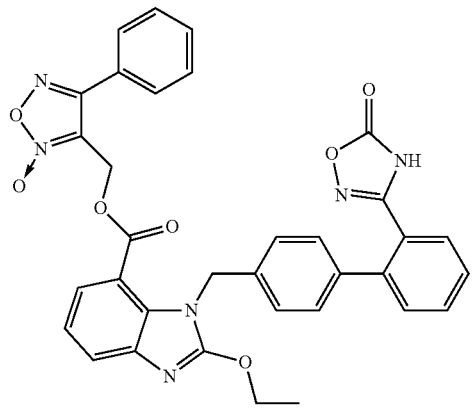
QR01009

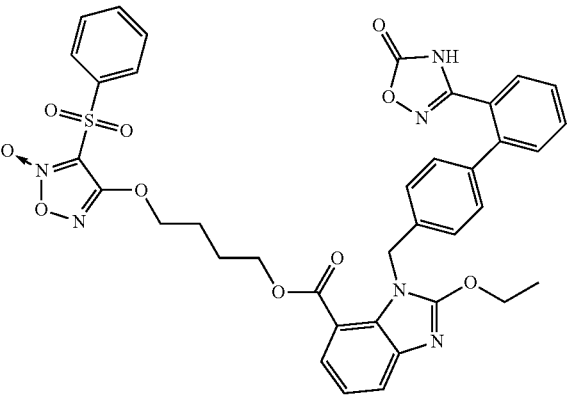
QR01011

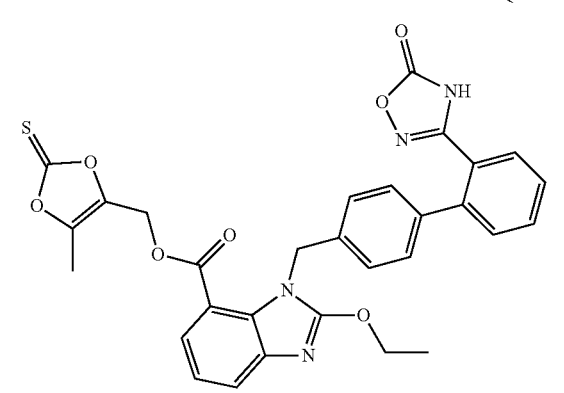
QR01013

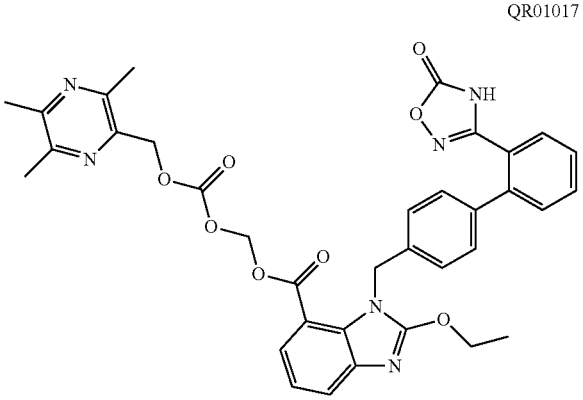
QR01017

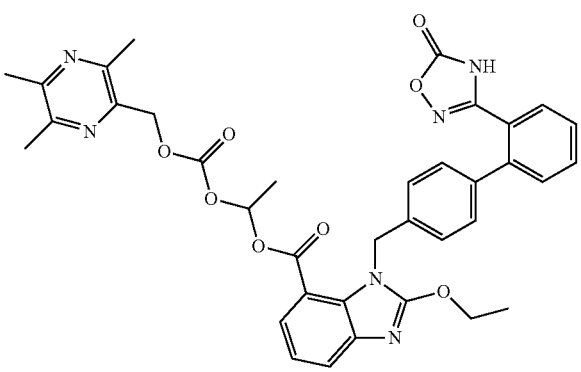
QR01019

QR01020
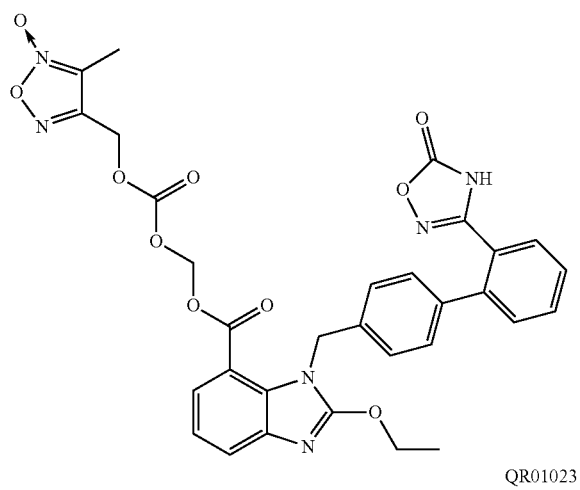
QR01023
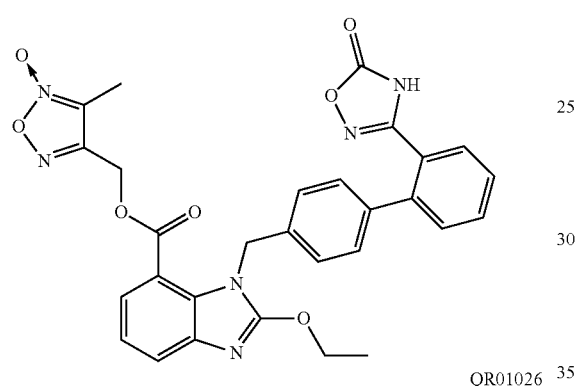
QR01026
QR01030
QR01031
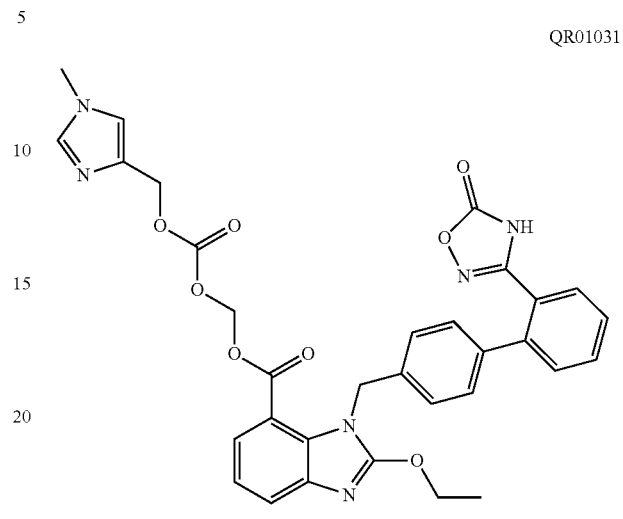
QR01032
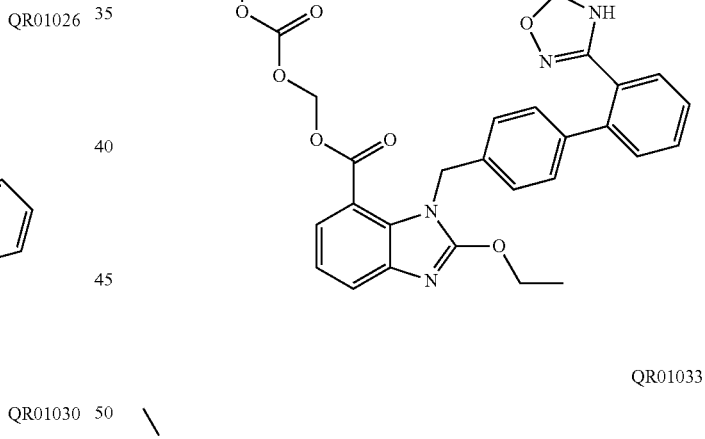
QR01033
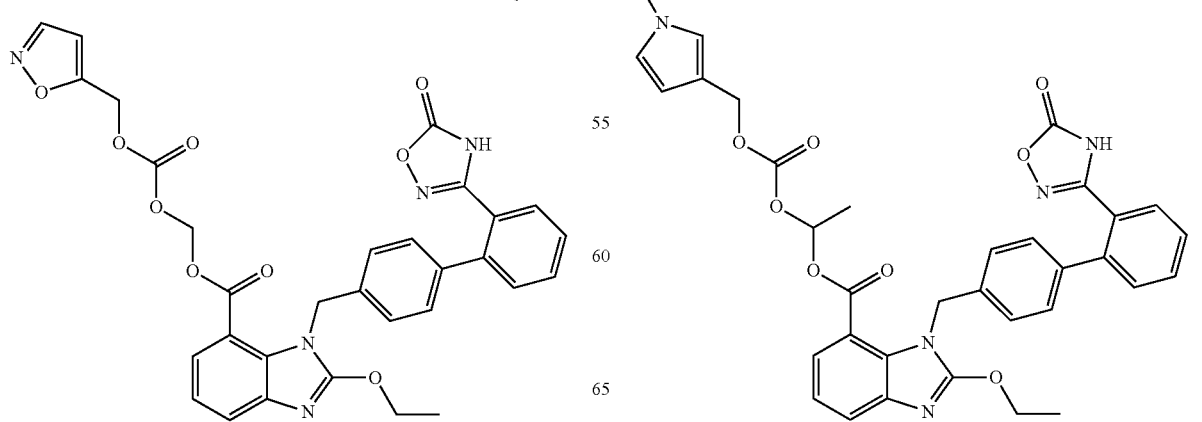

-continued
QR01034
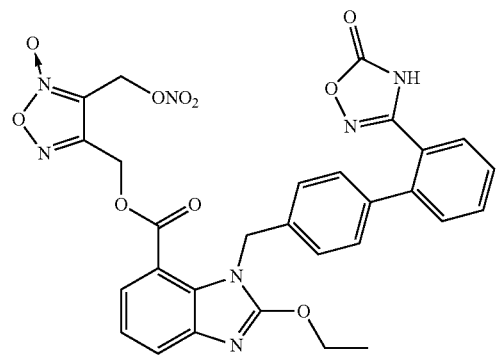
QR01035
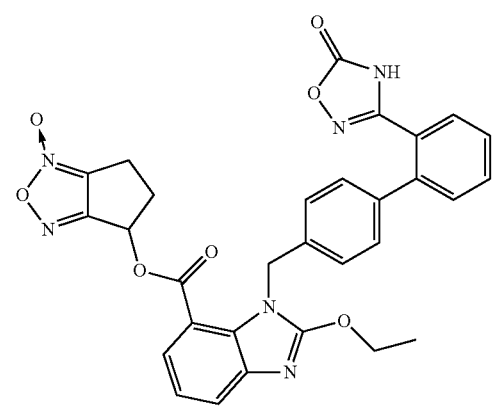
QR01036
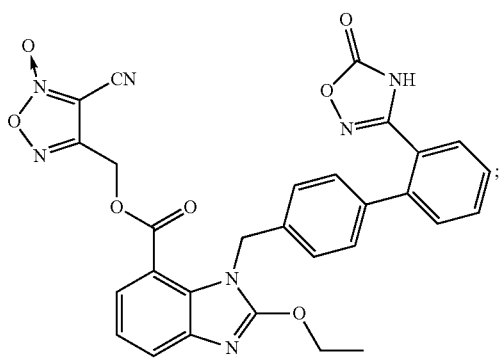
QR01005K
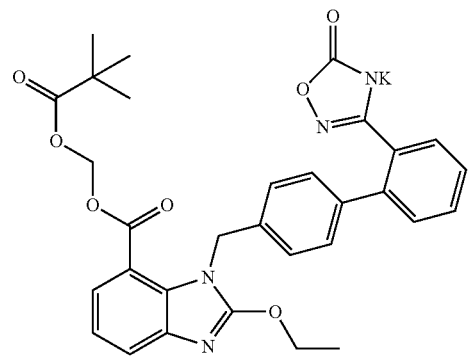
QR01008K
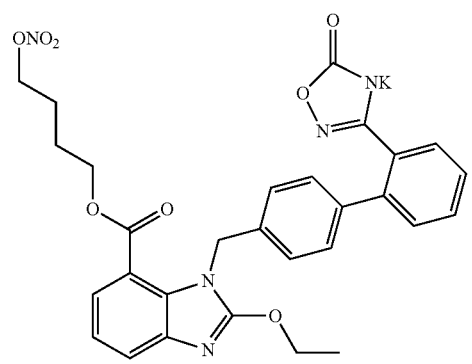
QR01009K
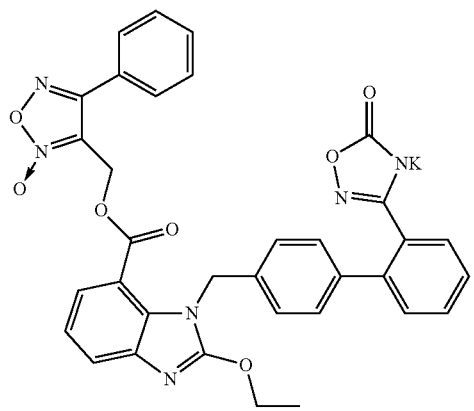
QR01011K
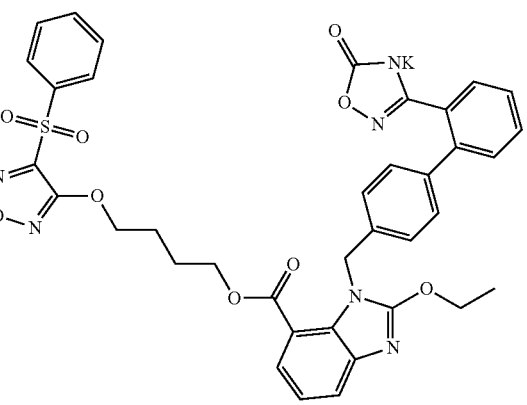
In a preferred embodiment, the compound of formula (II) has one of the structures shown below:

QR01013K
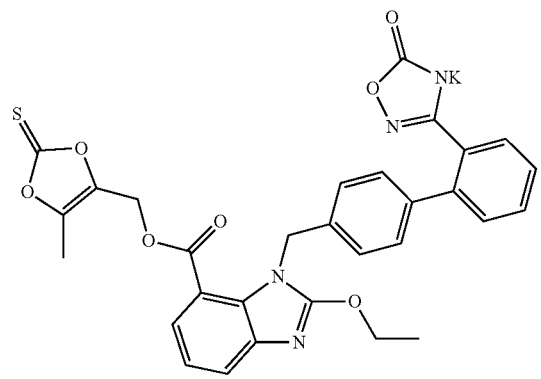
QR01017K
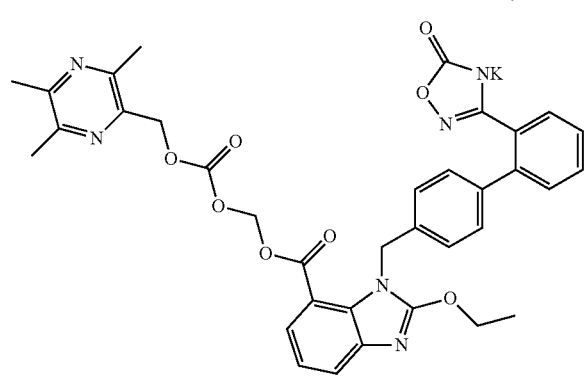
QR01019K
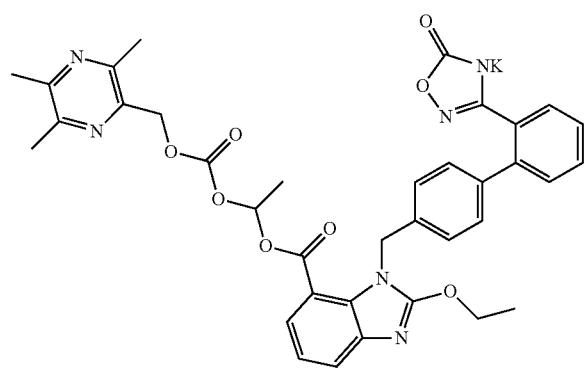
QR01020K
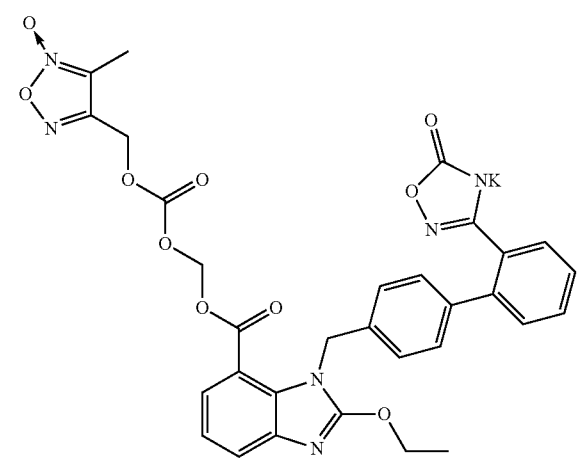
QR01023K
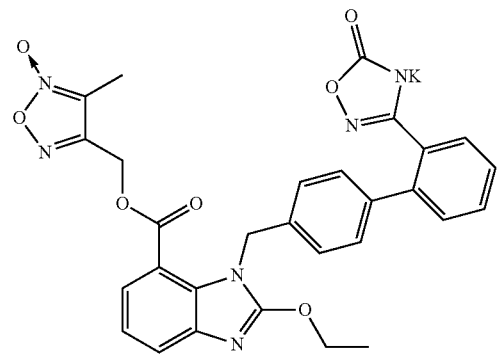
QR01026K
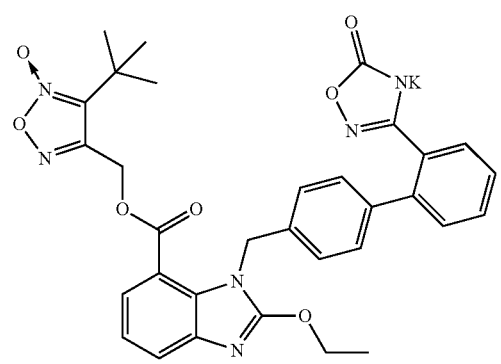
QR01030K
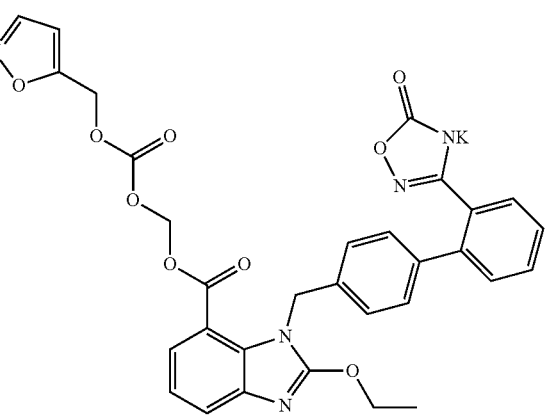
QR01031K
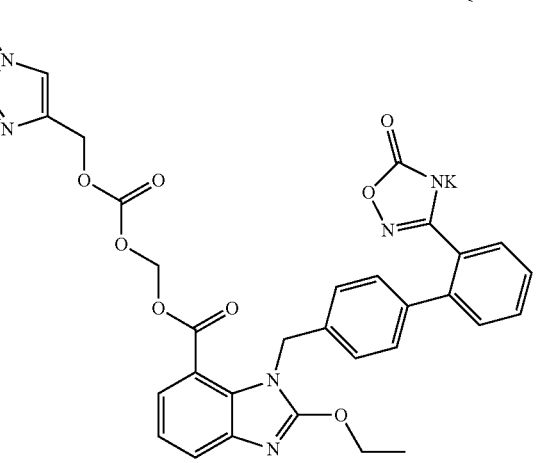

QR01032K

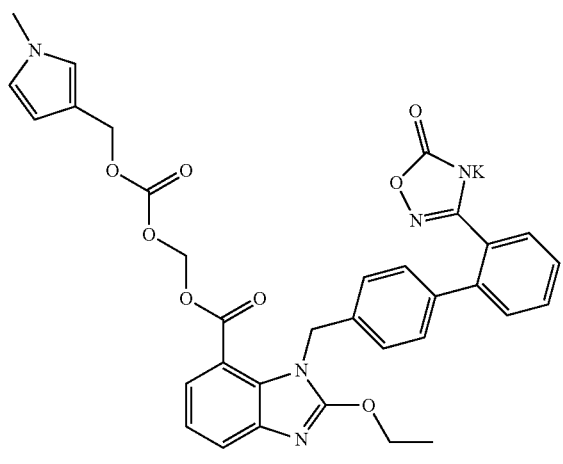

QR01035K

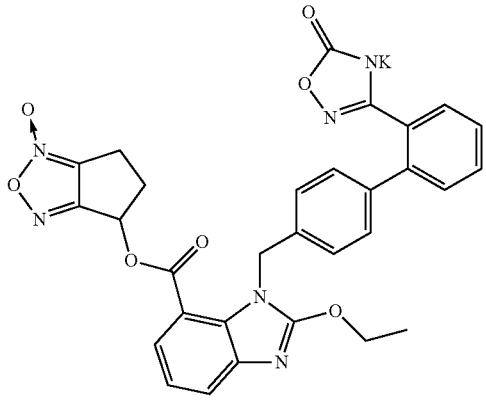

QR01036K

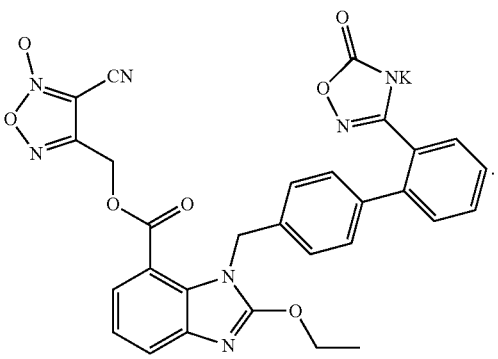

QR01033K

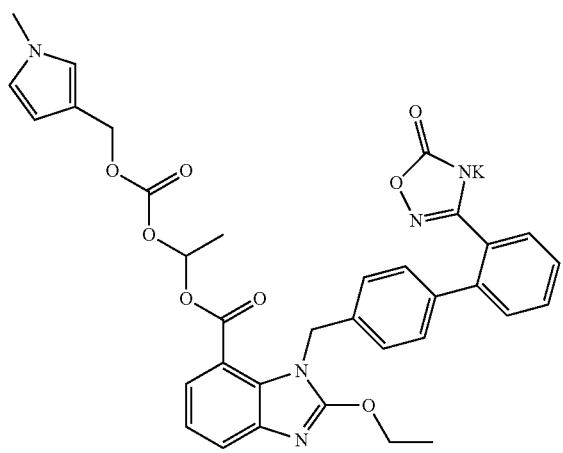

QR01034K

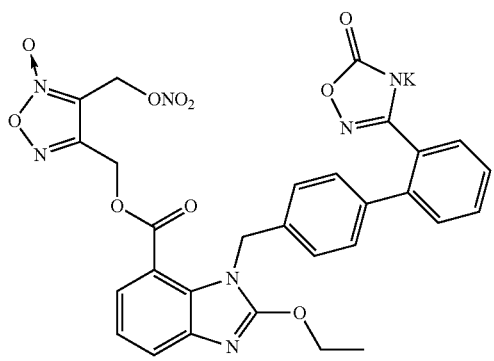

Wherein, the compound of formula (I) can be prepared by methods known in the art, such as those disclosed in CN 103709154 A. CN 103709154 A is incorporated herein in its entirety.

The compound of formula (II) can be prepared by reacting the compound of formula (I) with a potassium salt reagent. Preferably, the compound of formula (II) can be obtained as a reaction product of contacting the compound of formula (I) with a potassium salt reagent in a solvent.

It will be understood by those skilled in the art that various solvents can be used to prepare the compounds of formula (II). Preferably, the solvent is selected from at least one of polar solvents and non-polar solvents, or the solvent is selected from at least one of the group consisting of water, ether (for example, ether of 1-6 carbon atoms, ether of 1-6 carbon atoms substituted by hydroxyl or 3-8 membered cyclic ether), ketone (for example, ketone of 1 to 6 carbon atoms), alcohol (for example, monohydric alcohol, diol, or triol, which have 1 to 6 carbon atoms), ester, aromatic solvent, alkane (including cycloalkane) solvent, nitrile solvent, and sulfone. More preferably, the solvent is selected from at least one of the group consisting of methanol, ethanol, n-propanol, isopropanol, n-butanol, isobutanol, tert-butanol, methyltetrahydrofuran, tetrahydrofuran, 1,4-dioxane, glycol dimethyl ether, methyl tert-butyl ether, acetone, methyl ethyl ketone, 4-methyl-2-pentanone, ethyl acetate, n-propyl acetate, isopropyl acetate, n-butyl acetate, isobutyl acetate, sec-butyl acetate, tert-butyl acetate, dichloromethane, 1,2-dichloroethane, chloroform, carbon tetrachloride, nitroethane, N,N-dimethylformamide, dimethyl sulfoxide, acetonitrile, malononitrile, benzene, toluene, xylene, n-hexane, cyclohexane, pentane and n-heptane. It will be understood by those skilled in the art that the reaction between the compound of formula (I) and the potassium salt may still occur even if the compound of formula (I) is not completely dissolved in a solvent or even no solvent is present at all. Therefore, the solvent can be omitted or can be used in any amount.

In a preferred embodiment, the amount of solvent used per gram of the compound of formula (I) is at least about 0.1 ml, further preferably from about 2 ml to 300 ml, more preferably from about 5 ml to 100 ml, and most preferably from about 10 ml to 50 ml.

The potassium salt reagent is selected from at least one of the group consisting of potassium salt of organic acid and potassium salt of inorganic acid. Preferably, the potassium salt of organic acid is selected from at least one of the group consisting of potassium hydrogen phthalate, potassium acetate, potassium formate, potassium di-tert-butyl phosphate, dipotassium glycyrrhizinate, potassium 2-ethylhexanoate, potassium ethylxanthate, potassium sorbate, potassium phthalimide, potassium maleimide, potassium oxalate, potassium olefinate, potassium citrate, potassium malate, potassium gluconate, potassium lactate, potassium tartrate, potassium salicylate, potassium fumarate, potassium stearate and potassium laurate; the potassium salt of inorganic acid is selected from at least one of the group consisting of potassium nitrate, potassium sulfate, potassium sulfite, potassium bromate, potassium hydrogencarbonate, potassium thiocyanate, dipotassium hydrogenphosphate, potassium dihydrogen phosphate, and potassium hydrogen phthalate. The potassium olefinate is selected from potassium olefinate with 3 or more than 3 carbon atoms, preferably potassium olefinate of $C_3$-$C_{26}$, such as potassium acrylate, potassium crotonate, potassium octadecenoate and the like.

It can be understood by those skilled in the art that the potassium salt reagent can be dissolved or not be dissolved in the above solvent beforehand. In addition, some potassium salt reagents are stored in a solvent for unstable or dangerous nature, which accordingly can be employed directly. In a preferred embodiment, a molar ratio of the compound of formula (I) to potassium in the potassium salt reagent is from about 1:0.3 to 3, more preferably from about 1:0.9 to about 2, and most preferably from about 1:0.95 to about 1.5.

In a preferred embodiment, the compound of formula (I) is firstly placed in a solvent and then added with a potassium salt reagent. Preferably, the compound of formula (I) is placed in a solvent at a temperature between room temperature and a reflux temperature of the solvent; further preferably, after the potassium salt reagent is added, the temperature may be between 0° C. and the reflux temperature of the solvent; more preferably the temperature is between room temperature and the reflux temperature of the solvent. The term "room temperature" refers to from about 18° C. to about 30° C., preferably from about 20° C. to about 24° C., and more preferably about 22° C.

It will be understood by those skilled in the art that according to embodiments of the present disclosure, in terms of different solubility of the product in different solvents and different temperatures after completion of different reaction systems, the product may be dissolved in the solution or may be directly precipitated from the solution. In the case where the product is directly precipitated from the solution, the compound of the formula (II) is obtained by filtration and drying after completion of the reaction. Preferably, the solution is cooled before filtration to a temperature from about −50° C. to about 30° C., more preferably from about −10° C. to about 10° C., and most preferably from about 0° C. to about 5° C. In the case where the product is dissolved in the solution, impurities are removed by filtration as well as the solvent in the solution is removed to obtain the compound of the formula (II), or an anti-solvent is added to the solution, which is then filtered, and dried to give the compound of the formula (II) after the completion of the reaction. The means of removing the solvent comprises, for example, spin-drying or the like. Preferably, the solution is cooled before filtration to a temperature from about −50° C. to about 30° C., more preferably from about −10° C. to about 10° C., and most preferably from about 0° C. to about 5° C. Preferably, the anti-solvent is selected from reagents in which the solubility of the product is inferior to that in the selected reaction solvent, such as selected from at least one of the group consisting of methyltetrahydrofuran, tetrahydrofuran, 1,4-dioxane, glycol dimethyl ether, methyl tert-butyl ether, isopropyl ether, diethyl ether, dichloromethane, 1,2-dichloroethane, chloroform, carbon tetrachloride, nitroethane, n-hexane, cyclohexane, pentane, n-heptane, benzene, toluene and xylene.

In a more preferred embodiment, the active substance (active ingredient) is QR01019 or QR01019K as shown below:

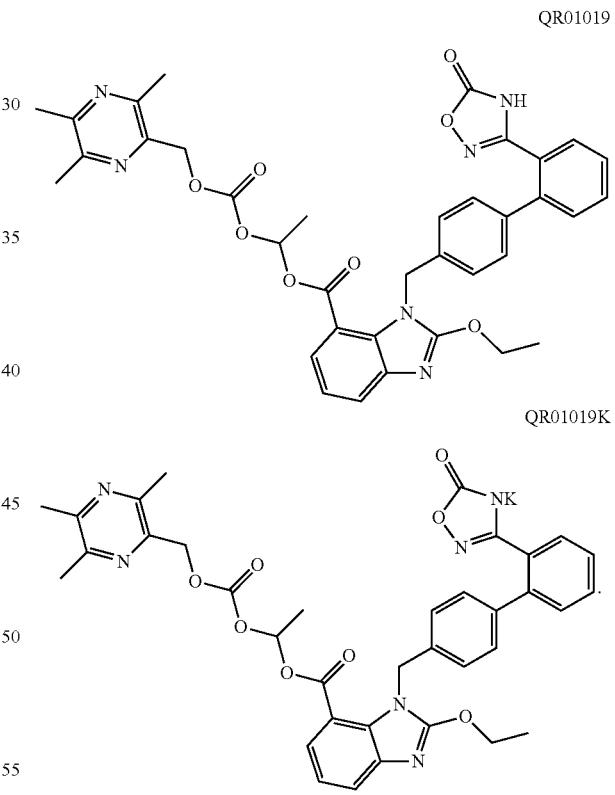

It will be understood by those skilled in the art that the complex disintegrant system provided by embodiments of the present disclosure is suitable for various active substances (active ingredients) because it can rapidly disintegrate the oral solid preparation, and the above active substances are not limited to the compound of formula (I) and formula (II).

The complex disintegrant system provided by embodiments of the present disclosure is suitable for the preparation of oral solid preparations, including tablets, capsules, powders, granules, dropping pills, films, and the like. In a preferred embodiment, the complex disintegrant system provided by embodiments of the present invention is particularly suitable for the preparation of tablets.

An embodiment of the present disclosure provides an oral solid preparation comprising an active substance (active ingredient), a complex disintegrant system as described above, an excipient and a lubricant. Preferably, a content of the active substance (active ingredient) is about 5-50% by weight, a content of the disintegrant is about 1-20% by weight, a content of the disintegrant assistant is about 0.1-35% by weight, a content of the excipient is about 20-80% by weight, a content of the lubricant is about 0.25-10% by weight, and a weight ratio of the disintegrant to the disintegrant assistant is from 10:1 to 1:10.

Further preferably, the content of the active substance (active ingredient) is about 8-30% by weight, the content of the disintegrant is about 2-18% by weight, the content of the disintegrant assistant is about 0.5-30% by weight, the content of the excipient is about 30-80% by weight, the content of the lubricant is about 0.5-8% by weight, and the weight ratio of the disintegrant to the disintegrant assistant is from 8:1 to 1:8. More preferably, the content of the active substance (active ingredient) is about 10-20% by weight, the content of the disintegrant is about 4-15% by weight, the content of the disintegrant assistant is about 1-25% by weight, the content of the excipient is about 50-80% by weight, the content of the lubricant is about 1-5% by weight, and the weight ratio of the disintegrant to the disintegrant assistant is from 5:1 to 1:5.

Most preferably, the content of the active substance (active ingredient) is about 12-16% by weight, the content of the disintegrant is about 6-10% by weight, the content of the disintegrant assistant is about 2-5% by weight, the content of the excipient is about 65-78% by weight, and the content of the lubricant is about 2-4%.

In an embodiment of the present disclosure, the active substance (active ingredient) is not particularly limited. Preferably, the active substance (active ingredient) is an active substance (ingredient) which can not be effectively disintegrated by any conventional disintegrant agent, for example, the active substance (active ingredient) is highly hygroscopic and becomes sticky after moisture absorption. Further preferably, the active substance (active ingredient) is selected from the compound of formula (I) and the compound of formula (II). More preferably, the active substance (active ingredient) is selected from QR01005, QR01008, QR01009, QR01011, QR01013, QR01017, QR01019, QR01020, QR01023, QR01026, QR01030, QR01031, QR01032, QR01033, QR01034, QR01035, QR01036, QR01005K, QR01008K, QR01009K, QR01011K, QR01013K, QR01017K, QR01019K, QR01020K, QR01023K, QR01026K, QR01030K, QR01031K, QR01032K, QR01033K, QR01034K, QR01035K, and QR01036K. Most preferably, the active substance (active ingredient) is QR01019 or QR01019K.

In embodiments of the present disclosure, the excipient is not particularly limited. Preferably, the excipient is selected from at least one of the group consisting of starch, lactose, mannitol, cellulose lactose, microcrystalline cellulose, calcium hydrogen phosphate and mannitol-starch complex.

In embodiments of the present disclosure, the lubricant is not particularly limited. Preferably, the lubricant is selected from at least one of the group consisting of talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

The oral solid preparation of embodiment of the present disclosure may further comprise a binder and/or a diluent depending on the nature of the active substance (active ingredient) and/or the preparation method.

In embodiments of the present disclosure, the binder is not particularly limited. Preferably, the binder is selected from at least one of the group consisting of starch and derivatives thereof (including but not limited to starch, pregelatinized starch, dextrin and maltodextrin, etc.), cellulose derivatives (including but not limited to methylcellulose, carboxy methylcellulose sodium, hydroxypropylcellulose, hypromellose, ethylcellulose and microcrystalline cellulose, etc.), natural and synthetic rubbers (including but not limited to gelatin, gum arabic, locust gum and peach glue, etc.), polyethylene glycol, povidone, glycerol dibehenate, carbomer, polyvinyl alcohol, poly(meth)acrylic resin, sugar alcohols (including but not limited to sucrose, liquid glucose, maltose alcohol, etc.), corn gluten, sodium alginate, and monolaurate. A suitable amount of the binder can be determined by those skilled in the art based on the active substance (active ingredient) and the properties of the excipients. Generally, the content of the binder is about 0-15%.

In embodiments of the present disclosure, the diluent is not particularly limited. Preferably, the diluent is selected from at least one of the group consisting of lactose (for example, monohydrate, spray dried monohydrate, anhydrate, and the like), mannitol, xylitol, glucose, sucrose, sorbitol, microcrystalline cellulose, starch and calcium hydrogen phosphate dihydrate. A suitable amount of the diluent can be determined by those skilled in the art based on the substance (active ingredient) and the properties of the excipients.

The oral solid preparation of the embodiments of the present disclosure may further optionally contains a surfactant, an antioxidant, a colorant, a flavoring agent, a preservative and/or a taste masking agent, and the like. The specific materials and suitable amounts of surfactants, antioxidants, colorants, flavoring agents, preservatives and/or taste masking agents can be selected by those skilled in the art based on the properties of the active substance (active ingredient) and the excipients.

The oral solid preparation of embodiment of the present disclosure may be a tablet, a capsule, a powder, a granule, a dropping pill, a film or the like. Preferably, the oral solid preparation of embodiments of the present disclosure is a tablet. The oral solid preparation of embodiments of the present disclosure can be used for the preparation of an angiotensin II receptor antagonist or for the preparation of a medicament for preventing and/or treating hypertension, chronic heart failure, and diabetic nephropathy.

An embodiment of the present disclosure provides an oral solid preparation comprising QR01019K and the complex disintegrant system. Preferably, the oral solid preparation further contains an excipient and a lubricant.

In the oral solid preparation of embodiments of the present disclosure, a content of QR01019K is about 5-50% by weight, a content of the disintegrant is about 1-20% by weight, a content of the disintegrant assistant is about 0.1-35% by weight, a content of the excipient is about 20-80% by weight, a content of the lubricant is about 0.25-10% by weight, and a weight ratio of the disintegrant to the disintegrant assistant is from 10:1 to 1:10. Preferably, the content of QR01019K is about 8-30% by weight, the content of the disintegrant is about 2-18% by weight, the content of the disintegrant assistant is about 0.5-30% by weight, the content of the excipient is about 30-80% by weight, the content of the lubricant is about 0.5-8% by weight, and the weight ratio of the disintegrant to the disintegrant assistant is from 8:1 to 1:8. More preferably, the content of QR01019K is about 10-20% by weight, the content of the disintegrant is about 4-15% by weight, the content of the disintegrant assistant is about 1-25% by weight, the content of the excipient is about 50-80% by weight, the content of the lubricant is about 1-5% by weight, and the weight ratio of the disintegrant to the disintegrant assistant is from 5:1 to 1:5. Most preferably, the content of QR01019K is about 12-16% by weight, the content of the disintegrant is about 6-10% by weight, the content of the disintegrant assistant is about 2-5% by weight, the content of the excipient is about 65-78% by weight, and the content of the lubricant is about 2-4% by weight.

In embodiments of the present disclosure, the excipient is not particularly limited. Preferably, the excipient is selected from at least one of the group consisting of starch, lactose, mannitol, cellulose lactose, microcrystalline cellulose, calcium hydrogen phosphate and mannitol-starch complex.

In embodiments of the present disclosure, the lubricant is not particularly limited. Preferably, the lubricant is selected from at least one of the group consisting of talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

The oral solid preparation of the embodiments of the present disclosure may further comprise a binder and/or a diluent depending on the nature of the active substance (active ingredient) and/or the preparation method.

In embodiments of the present disclosure, the binder is not particularly limited. Preferably, the binder is selected from at least one of the group consisting of starch and derivatives thereof (including but not limited to starch, pregelatinized starch, dextrin, maltodextrin, etc.), cellulose derivatives (including but not limited to methylcellulose, carboxy methylcellulose sodium, hydroxypropylcellulose, hypromellose, ethylcellulose and microcrystalline cellulose, etc.), natural and synthetic rubbers (including but not limited to gelatin, gum arabic, locust gum and peach glue, etc.), polyethylene glycol, povidone, glycerol dibehenate, carbomer, polyvinyl alcohol, poly(meth)acrylic resin, sugar alcohols (including but not limited to sucrose, liquid glucose and maltose alcohol, etc.), corn gluten, sodium alginate and monolaurate. A suitable amount of the binder can be determined by those skilled in the art based on the active substance (active ingredient) and the properties of the excipients. Generally, a content of the binder is about 0-15%.

In embodiments of the present disclosure, the diluent is not particularly limited. Preferably, the diluent is selected from at least one of the group consisting of lactose (for example, monohydrate, spray dried monohydrate, anhydrate, and the like), mannitol, xylitol, glucose, sucrose, sorbitol, microcrystalline cellulose, starch and calcium hydrogen phosphate dihydrate. A suitable amount of the diluent can be determined by those skilled in the art based on the properties of the active substance (active ingredient) and the excipients.

The oral solid preparation of embodiments of the present disclosure may further optionally contains a surfactant, an antioxidant, a colorant, a flavoring agent, a preservative and/or a taste masking agent, and the like. The specific materials and suitable amounts of surfactants, antioxidants, colorants, flavoring agents, preservatives and/or taste masking agents can be determined by those skilled in the art based on the properties of the active substance (active ingredient) and the excipients.

The oral solid preparation of embodiments of the present disclosure may be a tablet, a capsule, a powder, a granule, a dropping pill, a film or the like. Preferably, the oral solid preparation of embodiments of the present disclosure is a tablet. The oral solid preparation of embodiments of the present disclosure can be used for preparation of an angiotensin II receptor antagonist or for preparation of a medicament for preventing and/or treating hypertension, chronic heart failure, and diabetic nephropathy.

In an embodiment of the present disclosure, the unit dosage form of the oral solid preparation has a total weight of about 90 mg to 600 mg and a hardness of about 3 kg to 20 kg. The content of the active substance (active ingredient) QR01019K is about 10 mg to 100 mg per dosage unit.

In a most preferred embodiment, a tablet comprising QR01019K as an active active substance (active ingredient), mannitol as an excipient, croscarmellose sodium as a disintegrant, sodium hydrogencarbonate as a disintegrant assistant, and magnesium stearate as a lubricant is provided; preferably, a content of the active substance (active ingredient) QR01019K is about 5-50% by weight, a content of the disintegrant croscarmellose sodium is about 1-20%, a content of the disintegrant assistant sodium hydrogencarbonate is about 0.1-35%, a content of the excipient mannitol is about 20-80%, a content of the lubricant magnesium stearate is about 0.25-10%, and a weight ratio of the disintegrant to the disintegrant assistant is from 10:1 to 1:10. Further preferably, the content of the active substance (active ingredient) QR01019K is about 8-30% by weight, the content of the disintegrant croscarmellose sodium is about 2-18% by weight, the content of the disintegrant assistant sodium hydrogencarbonate is about 0.5-30% by weight, the content of the excipient mannitol is about 30-80% by weight, and the content of the lubricant magnesium stearate is about 0.5-8% by weight, and the weight ratio of the disintegrant to the disintegrant assistant is from 8:1 to 1:8. More preferably, the content of the active substance (active ingredient) QR01019K is about 10-20% by weight, the content of the disintegrant croscarmellose sodium is about 4-15% by weight, the content of the disintegrant assistant sodium hydrogencarbonate is about 1-25% by weight, the content of the excipient mannitol is about 50-80% by weight, the content of the lubricant magnesium stearate is about 1-5% by weight, and the weight ratio of the disintegrant to the disintegrant assistant is from 5:1 to 1:5. Most preferably, the content of the active substance (active ingredient) QR01019K is about 12-16% by weight, the content of the disintegrant croscarmellose sodium is about 6-10% by weight, the content of the disintegrant assistant sodium hydrogencarbonate is about 2-5% by weight, the content of the excipient mannitol is about 65-78% by weight, and the content of the lubricant magnesium stearate is about 2-4% by weight.

The complex disintegrant system of embodiments of the present disclosure can effectively promoting the collapse of the solid preparation as well as the drug release even if a large viscosity is produced by the contact of the active substance (active ingredient) with water (in which case the solid preparation cannot be disintegrated using conventional disintegrants).

The complex disintegrant system of embodiments of the present disclosure enables rapid disintegration and release of the active substance (active ingredient), thereby improving the bioavailability by using only an acidic environment, without additional acids.

By adding a soluble small molecule or a gas generating type salt, effective disintegration of the active substance (active ingredient) which is highly hygroscopic and becomes sticky after moisture absorption is achieved in embodiments of the present disclosure, thereby promoting the release of the active substance (active ingredient) and improving bioavailability.

The solid preparation of embodiments of the present disclosure can be used for prevention and/or treatment of hypertension, chronic heart failure, and diabetic nephropathy.

The solid preparation of embodiments of the present disclosure is administered by an oral route, which is convenient to use.

The complex disintegrant system of embodiments of the present disclosure can improve the drug-forming properties of the substance (active ingredient) and patient compliance.

BRIEF DESCRIPTION OF THE DRAWINGS

In order to clearly illustrate the technical solution of the embodiments of the disclosure, the drawings of the embodiments will be briefly described in the following, it is obvious that the described drawings are only related to some embodiments of the disclosure and thus are not limitative of the disclosure.

DETAILED DESCRIPTION OF THE INVENTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Example 1: Preparation of QR01019K

QR01019K (1.0 g) was dissolved in dichloromethane (5 ml), and the mixture was stirred at room temperature to form a solution, which was then added with potassium phthalimide (0.27 g), kept for 4 hours at room temperature, and cooled to −50° C., followed by filtration and solvent spin-drying to obtain an amorphous form of QR01019K.

Melting point: 135-145° C.

MS/HRMS m/z: 717 [M+H]$^+$; 677 [M−K]$^−$.

$^1$H-NMR (400 MHz, DMSO-$d_6$) δ: 1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

Figure 1:
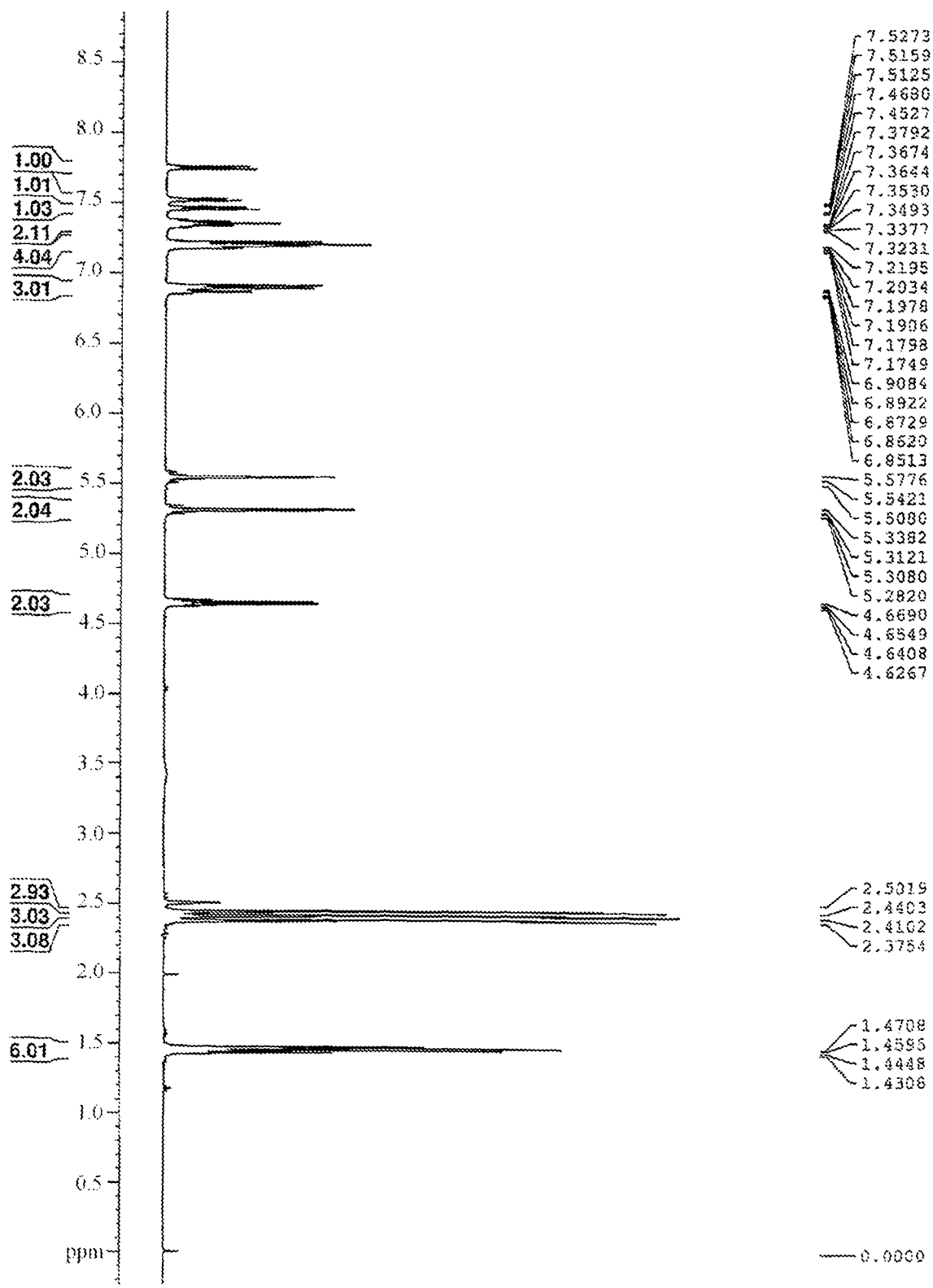
FIG. 1 is an H-NMR spectrum of QR01019K in example 1.
Figure 2:
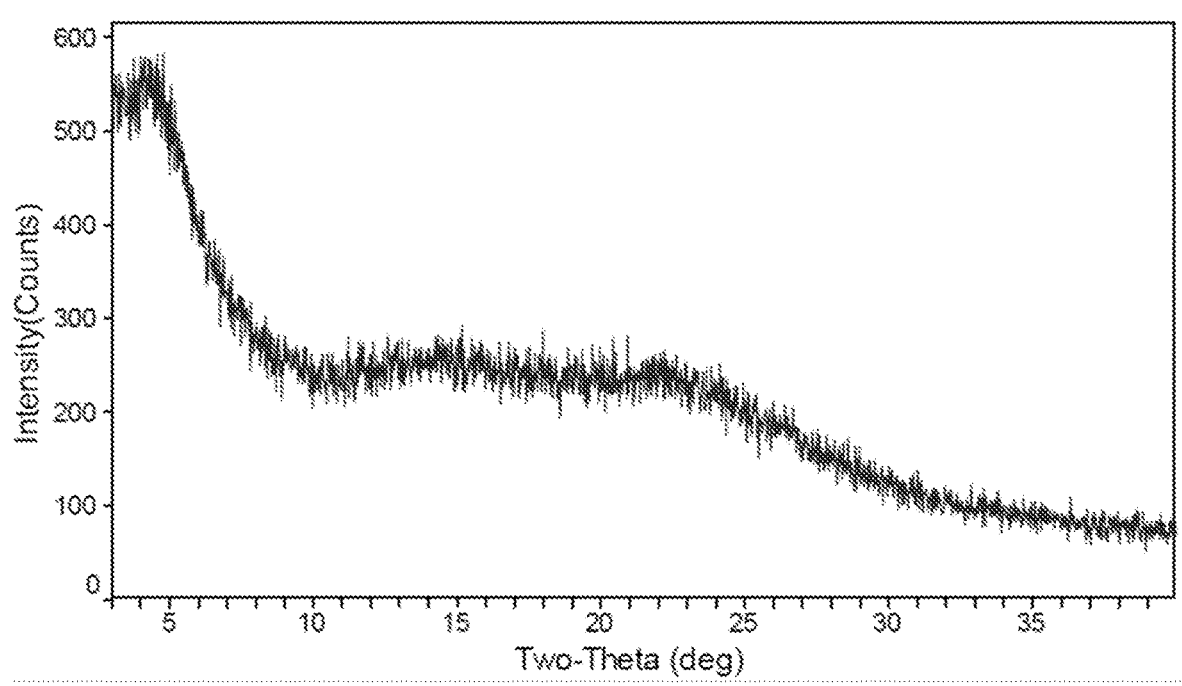
FIG. 2 is an X-ray powder diffraction pattern of QR01019K in example 1.

The $^1$H-NMR spectrum and the X-ray powder diffraction pattern are respectively shown in FIG. 1 and FIG. 2.

Example 2: Antihypertensive Efficacy Test of QR01019K in Spontaneously Hypertensive Rats 12-week-old spontaneously hypertensive rats (hereinafter referred to as SHR, purchased from Beijing Weitong Lihua Experimental Animal Technology Co., Ltd.) were anesthetized with 2.5% sodium pentobarbital for intraperitoneal injection. After that, the blood pressure sensing catheter of hypertension implant was inserted into their abdominal aorta, while the implant was fixed to the abdominal wall, and then postoperative daily care was performed after suturing. Rats with systolic blood pressure exceeding 160 mm Hg were divided into 3 groups (control group, QR01019 group and QR01019K group) wherein each group has 8 rats. The control group was administrated 0.5% sodium carboxymethylcellulose (hereinafter referred to as CMC-Na); QR01019 group and QR01019K group were respectively administered, both of which were dissolved by 0.5% CMC-Na, by intragastric administration, at a dose of 1 mg/kg (calculated by the effective dose of Azilsartan) and a volume calculated by 4 mL/kg. The systolic blood pressure and heart rate of SHR were compared before and after administration (the systolic blood pressure and heart rate of SHR before administration as reference value), which were detected three times at each time point with the average value recorded. The results are shown in Tables 1 and 2 below.

TABLE 1

Systolic blood pressure change at each time point before and after oral administration of QR01019 and QR01019K (average (mmHg) ± standard error)

| Group | Before administration | 1 hour after administration | 3 hours after administration | 5 hours after administration |
|---|---|---|---|---|
| Control group | 0.0 ± 0.0 | 5.4 ± 7.1 | −3.5 ± 4.6 | 4.5 ± 4.0 |
| QR01019 group | 0.0 ± 0.0 | −4.9 ± 4.8 | −22.0 ± 3.6* | −30.5 ± 3.5* |
| QR01019K group | 0.0 ± 0.0 | −7.0 ± 3.4 | −34.3 ± 1.9* | −46.5 ± 2.5* |

| Group | 7 hours after administration | 10 hours after administration | 24 hours after administration |
|---|---|---|---|
| Control group | 4.1 ± 3.2 | −2.9 ± 2.3 | −2.7 ± 6.4 |
| QR01019 group | −38.8 ± 2.3* | −33.0 ± 1.7* | −10.2 ± 2.1 |
| QR01019K group | −49.4 ± 4.1* | −45.3 ± 3.3* | −25.9 ± 3.4* |

*P < 0.01 (relative to the control group)

It can be seen from the results in Table 1 that after 3 hours of administration, the systolic blood pressure of the QR01019 group or the QR01019K group groups is significantly decreased compared with the control group, and the drug efficacy peaks 5-7 hours after administration, and the QR01019K group is more potent with a longer-lasting antihypertensive effect than the QR01019 group.

TABLE 2

Heart rates change before and after oral administration of QR01019 and QR01019K (average (times/minute) ± standard error)

| Group | Before administration | 1 hour after administration | 3 hours after administration | 5 hours after administration |
|---|---|---|---|---|
| Control group | 0.0 ± 0.0 | 0.14 ± 2.9 | 6.4 ± 2.8 | −0.3 ± 2.7 |
| QR01019 group | 0.0 ± 0.0 | −3.4 ± 2.6 | −2.33 ± 2.6* | −6.5 ± 2.8* |
| QR01019K group | 0.0 ± 0.0 | −3.6 ± 2.4 | −5.0 ± 2.5* | −10.1 ± 3.0* |

TABLE 2-continued

Heart rates change before and after oral administration of QR01019 and QR01019K (average (times/minute) ± standard error)

| Group | 7 hours after administration | 10 hours after administration | 24 hours after administration |
|---|---|---|---|
| Control group | −0.1 ± 2.9 | −2.5 ± 2.5 | 4.3 ± 2.8 |
| QR01019 group | −6.2 ± 3.0* | −12.3 ± 2.8* | −6.7 ± 2.6* |
| QR01019K group | −17.5 ± 3.0* | −25.4 ± 2.4* | −28.6 ± 8* |

*$P < 0.05$ (relative to the one-way ANOVA of the control group).

It can be seen from the results in Table 2 that after 3 hours of administration, the QR01019K group is more potent with a longer-lasting heart rate lowering effect, compared with the QR01019 group.

The pharmacodynamic tests of QR01005K, QR01008K, QR01009K, QR01011K, QR01013K, QR01017K, QR01020K, QR01023K, QR01026K, QR01030K, QR01031K, QR01032K, QR01033K, QR01034K, QR01035K, QR01036K were also tested in the same manner as above, and these compounds were found to be similar to QR01019K, all of which have a more potent and longer-lasting antihypertensive and heart rate lowering effect than their corresponding unsalted compounds.

Example 3: Preparation and Disintegration Experiment of an Oral Solid Preparation The tablets of preparation examples 1-11 and comparative examples 1-11 were prepared according to the following three preparation methods. The formula composition and differences in tablet hardness and tablet weight of each preparation example and each comparative example were shown in Table 3 below.

Preparation examples 1, 7, 8, 9 as well as comparative examples 1, 7, 8, 9 employed a powder tabletting method: a 60-mesh sieve was selected according to the material properties, and the materials were sieved for use (in preparation example 7 and comparative example 7, the active ingredients were sifted together with the excipients, besides, the disintegrant and the disintegrant assistant were mixed together and sieved for use; while in the other preparation examples and comparative examples, above components were sieved separately); the active ingredient, the excipient, the disintegrant, and the disintegrant assistant (which was not added in comparative examples) were poured into a three-dimensional mixer for mixing, and then added with a lubricant for final mixing; the final mixed material was tabletted in a rotary tabletting machine.

A wet granulation method is employed in preparation examples 2, 4, 5, 10 as well as comparative examples 2, 4, 5, 10: a 60 mesh sieve was selected according to the material properties, and the materials were sieved for use; the active ingredient, the excipient, the disintegrant, and the disintegrant assistant (which was not added in comparative examples) were poured into a granulator, mixed together, added with an aqueous solution of the binder (5% aqueous solution of povidone was used in preparation example 2 and comparative example 2, 10% starch slurry was used in preparation example 4 and comparative example 4, and 8% starch slurry was used in preparation example 5 and comparative example 5), granulated and dried in fluidized bed; the dried granules were placed in a three-dimensional mixer, and then added with a lubricant for final mixing; the final mixed material was tabletted in a rotary tablet press.

A dry granulation method is employed in preparation examples 3, 6, 11 as well as comparative examples 3, 6, 11: a 60 mesh sieve was selected according to the material properties, and the materials were sieved for use; the active ingredient, the excipient, the disintegrant and the disintegrant assistant (which was not added in comparative examples) were poured into a three-dimensional mixer for mixing, and granulated in a dry granulator; the obtained granules were placed in a three-dimensional mixer, and then added with a lubricant for final mixing; the final mixed material was tabletted in a rotary tablet press.

The disintegration experiments were carried out according to the following experimental conditions, and the disintegration time of each preparation example and comparative example is shown in Table 3 below.

Instrument: ZBS-6E intelligent disintegration tester (Tianjin Tianda Tianfa Technology Co., Ltd.)
Method: hanging basket method
Medium: 0.1 M HCl medium containing 0.5% Tween 80
Round trip frequency: 30-32 times per minute
Temperature: 37° C.

TABLE 3

Tablet formula and disintegration time

| | | ingredient content/(mg/tablet) in comparative examples | | | | | | | | | | |
|---|---|---|---|---|---|---|---|---|---|---|---|---|
| | formula composition | 1 | 2 | 3 | 4 | 5 | 6 | 7 | 8 | 9 | 10 | 11 |
| active integrant | QR01019K | 21 | 24 | 30 | 17 | 21 | 21 | 21 | 21 | 21 | 21 | 21 |
| excipient | lactose | | 125 | | | | | | | | | |
| | mannitol | 50 | | | | | 110 | 156 | 108 | | 117 | 137 | 137 |
| | cellulose lactose | | | 120 | 60 | | | | | | | 20 |
| | microcrystalline cellulose | 11 | | | | 30 | | | | | | |
| | mannitol-starch | | | | | | | | | 100 | | |
| disintegrant | cross-linked sodium carboxymethyl cellulose | 8 | 15 | 25 | | | | 12 | | | | |
| | cross-linked povidone | | | | 6 | | 16 | | 10 | 10 | 10 | 10 |
| | low substituted hydroxypropyl cellulose | | | | | 15 | | | | | | |
| binder | povidone | | 15 | | | | | | | | | |
| | starch | | | | 10 | 10 | | | | | | |

TABLE 3-continued

Tablet formula and disintegration time

| | | | | | | | | | | | | |
|---|---|---|---|---|---|---|---|---|---|---|---|---|
| disintegrant assitant | sodium bicarbonate | | | | | | | | | | | |
| | sodium carbonate | | | | | | | | | | | |
| | magnesium carbonate | | | | | | | | | | | |
| | sodium glycine carbonate | | | | | | | | | | | |
| | sodium sesquicarbonate | | | | | | | | | | | |
| | sodium chloride | | | | | | | | | | | |
| | glucose | | | | | | | | | | | |
| lubricant | magnesium stearate | 3 | 6 | 5 | 3 | | | 4.5 | | 2 | 2 | 2 |
| | sodium stearyl fumarate | | | | | 5 | 8 | | 6 | | | |
| tablet hardness (kg/mm$^2$) | | 3-10 | 3-10 | 4-6 | 4-6 | 4-6 | 4-6 | 3-10 | 4-6 | 4-6 | 4-6 | 4-6 |
| tablet weight difference (within %) | | ±5 | ±5 | ±5 | ±5 | ±5 | ±5 | ±5 | ±5 | ±5 | ±5 | ±5 |
| disintegration time | | >15 min | >15 min | >15 min | >15 min | >15 min | >15 min | >15 min | >15 min | >15 min | >15 min | >15 min |

| | | ingredient content/(mg/tablet) in preparation examples | | | | | | | | | | |
|---|---|---|---|---|---|---|---|---|---|---|---|---|
| | formula composition | 1 | 2 | 3 | 4 | 5 | 6 | 7 | 8 | 9 | 10 | 11 |
| active integrant | QR01019K | 21 | 24 | 30 | 17 | 21 | 21 | 21 | 21 | 21 | 21 | 21 |
| excipient | lactose | | 125 | | | | | | | | | |
| | mannitol | 50 | | | | 110 | 156 | 108 | | 117 | 137 | 137 |
| | cellulose lactose | | | 120 | 60 | | | | | | | 20 |
| | microcrystalline cellulose | 11 | | | 30 | | | | | | | |
| | mannitol-starch | | | | | | | | | 100 | | |
| disintegrant | cross-linked sodium carboxymethyl cellulose | 8 | 15 | 25 | | | | 12 | | | | |
| | cross-linked povidone | | | | 6 | | 16 | | 10 | 10 | 10 | 10 |
| | low substituted hydroxypropyl cellulose l | | | | | 15 | | | | | | |
| binder | povidone | | 15 | | | | | | | | | |
| | starch | | | | | 10 | 10 | | | | | |
| disintegrant assitant | sodium bicarbonate | 8 | | | | | | 4.5 | 15 | | | 10 |
| | sodium carbonate | | 15 | | | | 15 | | | | | |
| | magnesium carbonate | | | | | 9 | | | | | | |
| | sodium glycine carbonate | | | 20 | | | | | | | | |
| | sodium sesquicarbonate | | | | 4 | | | | | | | |
| | sodium chloride | | | | | | | | | 50 | | 20 |
| | glucose | | | | | | | | | | 30 | |
| lubricant | magnesium stearate | 3 | 6 | 5 | 3 | | | 4.5 | | 2 | 2 | 2 |
| | sodium stearyl fumarate | | | | | 5 | 8 | | 6 | | | |
| tablet hardness (kg/mm$^2$) | | 3-10 | 3-10 | 4-6 | 4-6 | 4-6 | 4-6 | 3-10 | 4-6 | 4-6 | 4-6 | 4-6 |
| tablet weight difference (within %) | | ±5 | ±5 | ±5 | ±5 | ±5 | ±5 | ±5 | ±5 | ±5 | ±5 | ±5 |
| disintegration time | | <60 s | <60 s | <60 s | <60 s | <60 s | <60 s | <60 s | <60 s | <120 s | <120 s | <120 s |

What is claimed is:

1. An oral solid preparation comprising an active ingredient, a complex disintegrant system, an excipient and a lubricant;

wherein the active ingredient is selected from the group consisting of compounds of following formula (I) and formula (II):

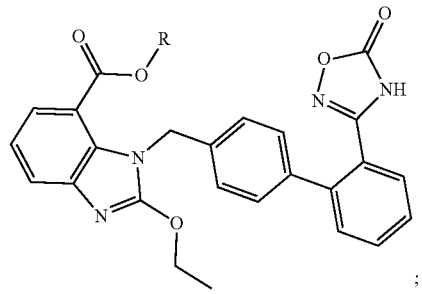
(I)

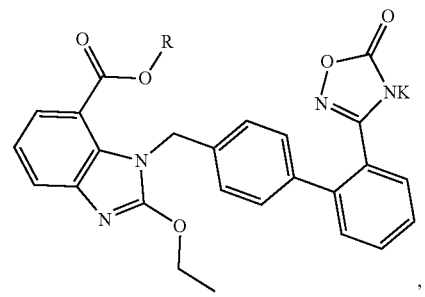
(II)

wherein in formula (I) and formula (II), R represents

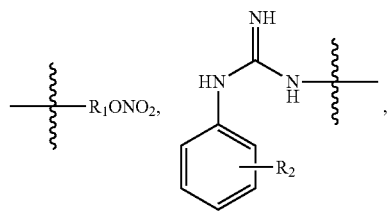

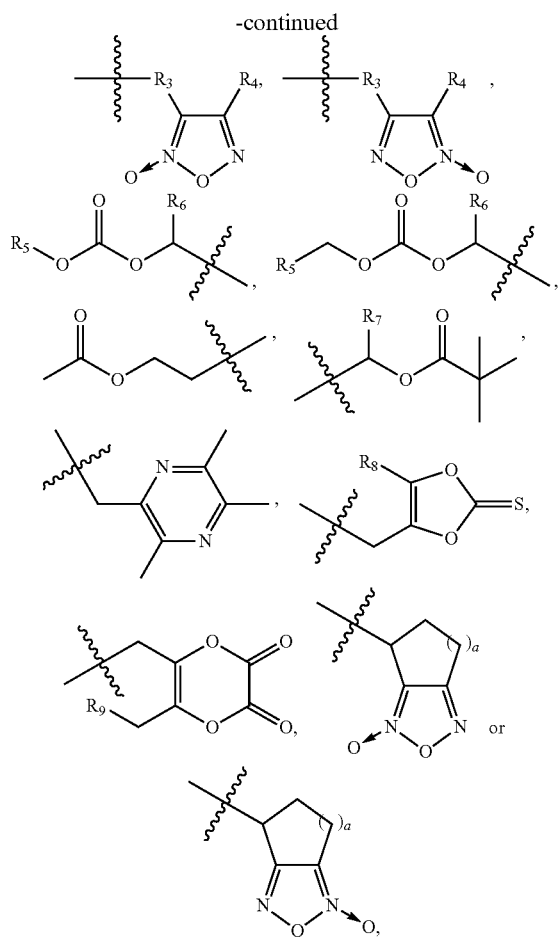

wherein, a=0, 1, 2, 3, 4, 5 or 6;
wherein, $R_1$ represents $C_2$-$C_8$ alkyl, $C_2$-$C_8$ alkene, $C_2$-$C_8$ alkyne,

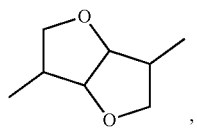

$(CH_2)_nO(CH_2)_m$,

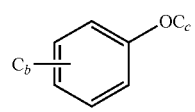

phenyl, substituted phenyl, heteroaryl group or substituted heteroaryl group, wherein, $C_b$, $C_c$ in

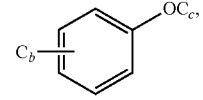

independently represent H or alkyl, wherein, b, c represent a number of carbon atoms, and are each independently selected from 0, 1, 2, 3, 4, 5 or 6;
wherein n, m in $(CH_2)_nO(CH_2)_m$ are each independently selected from 1, 2, 3, 4, 5 or 6;
wherein $R_2$ represents hydrogen, halogen, trifluoromethyl, $C_1$-$C_8$ alkoxy, $C_1$-$C_8$ alkyl, nitro, sulfonamide, amino or nitrile;
wherein $R_3$ represents $C_1$-$C_8$ alkyl, $C_1$-$C_8$ alkoxy, $C_2$-$C_8$ alkeneoxy, $C_2$-$C_8$ alkyneoxy, $(C_1$-$C_6)O(C_1$-$C_6)$,

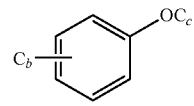

phenyl, substituted phenyl, heteroaryl group or substituted heteroaryl group, wherein, $C_b$, $C_c$ in

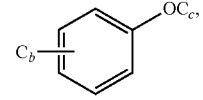

independently represent H or alkyl, wherein, b, c represent a number of carbon atoms, and are each independently selected from 0, 1, 2, 3, 4, 5 or 6;
wherein $R_4$ represents phenyl, substituted phenyl, benzenesulfonyl, 5-6 membered heteroaryl group, 5-6 membered substituted heteroaryl group, nitrile, trifluoromethyl, $C_1$-$C_8$ alkoxy, $C_1$-$C_8$ nitrate, $C_1$-$C_8$ alkyl;
wherein $R_5$ represents phenyl, substituted phenyl, 5-6 membered heteroaryl group, 5-6 membered substituted heteroaryl group, nitrile, trifluoromethyl, $C_1$-$C_8$ alkoxy, $C_1$-$C_8$ nitrate, $C_1$-$C_8$ alkyl, $C_1$-$C_8$ alkene, $C_1$-$C_8$ alkyne,

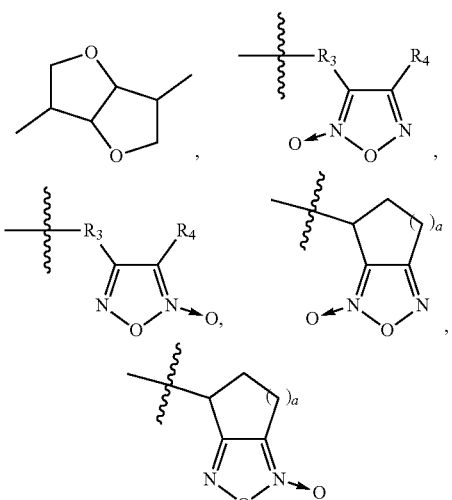

or $(CH_2)_nO(CH_2)_m$, wherein $R_3$, $R_4$, a, m, n are as defined above;
wherein $R_6$ and $R_7$ represent hydrogen, $C_1$-$C_8$ alkoxy or $C_1$-$C_8$ alkyl;
wherein $R_8$ and $R_9$ represent hydrogen, $C_1$-$C_8$ alkoxy, $C_1$-$C_8$ nitrate or $C_1$-$C_8$ alkyl;

wherein the substituted phenyl refers to phenyl substituted by one or more selected from the group consisting of hydroxyl, $C_1$-$C_6$ alkyl, $C_1$-$C_6$ alkoxy, halogen, nitro, amino, nitrile, trifluoromethyl and —CH=CHCO$_2$R$_{11}$, wherein each substituent may be same or different, wherein $R_{11}$ represents hydrogen or $C_1$-$C_6$ alkyl;

wherein the heteroaryl group refers to a -5-7 membered aryl group having 1 to 4 hetero atoms, each of which is independently selected from O, S or N;

wherein the substituted heteroaryl group is a heteroaryl group substituted by at least one selected from the group consisting of $C_1$-$C_6$ alkyl, $C_1$-$C_6$ alkoxy and halogen, wherein each substituent may be same or different;

wherein the complex disintegrant system consists of a disintegrant and a disintegrant assistant, the disintegrant being a hygroscopic swelling type disintegrant and the disintegrant assistant being a soluble small molecule or a gas generating type salt;

wherein the hygroscopic swelling type disintegrant is selected from at least one of the group consisting of dry starch, croscarmellose sodium, sodium carboxymethylcellulose, calcium carboxymethylcellulose, sodium carboxymethyl starch, methylcellulose, low substituted hydroxylpropyl cellulose, crospovidone, chitosan, and microcrystalline cellulose;

wherein the gas generating salt is selected from at least one of the group consisting of sodium carbonate, potassium carbonate, zinc carbonate, magnesium carbonate, ammonium carbonate, sodium glycine carbonate, sodium sesquicarbonate, sodium hydrogencarbonate, potassium hydrogencarbonate, and ammonium hydrogencarbonate;

wherein the soluble small molecule is selected from at least one of the group consisting of sodium chloride, glucose, fructose, and xylitol;

wherein the content of the active ingredient is about 10-20% by weight, the content of the disintegrant is about 4-15% by weight, the content of the disintegrant assistant is about 1-25% by weight, the content of the excipient is about 50-80% by weight, the content of the lubricant is about 1-5% by weight, and the weight ratio of the disintegrant to the disintegrant assistant is from 5:1 to 1:5.

2. The oral solid preparation according to claim 1, wherein the compound of formula (I) has one of structures shown below:

QR01005

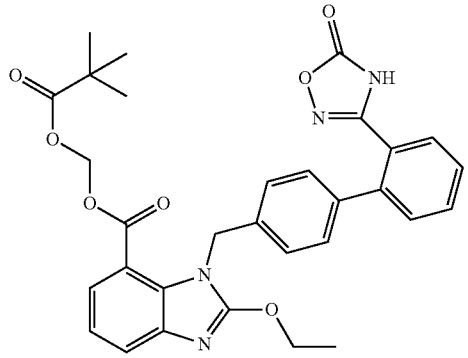

QR01008

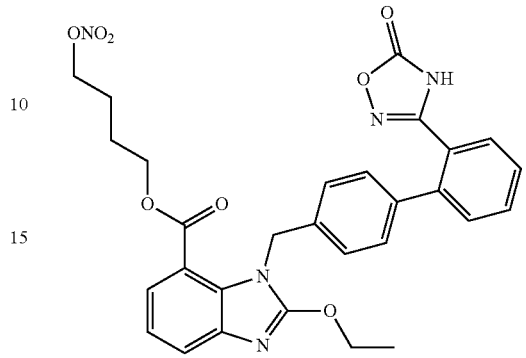

QR01009

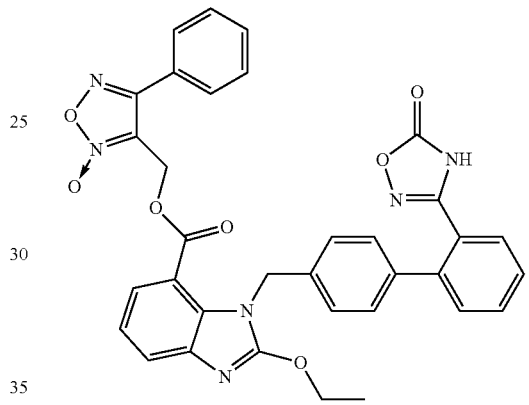

QR01011

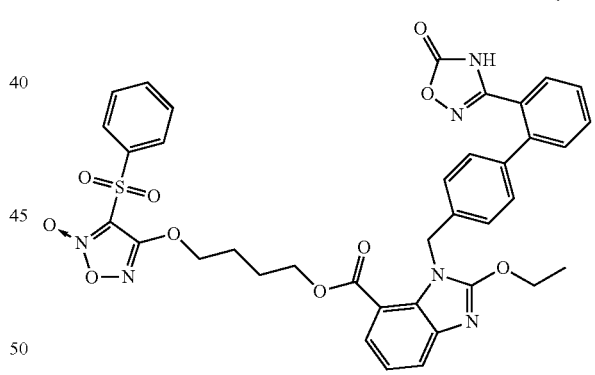

QR01013

33
-continued
QR01017
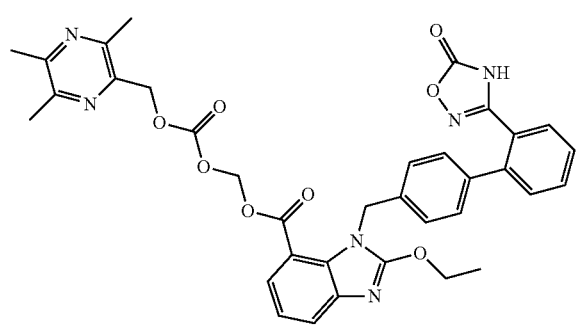
QR01019
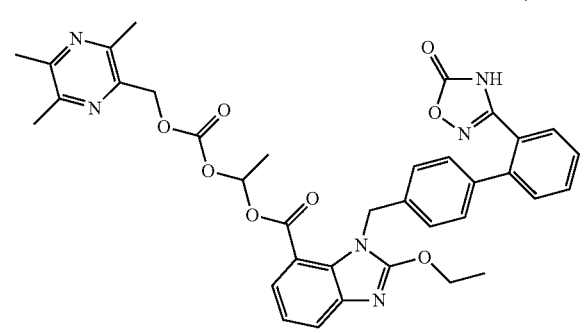
QR01020
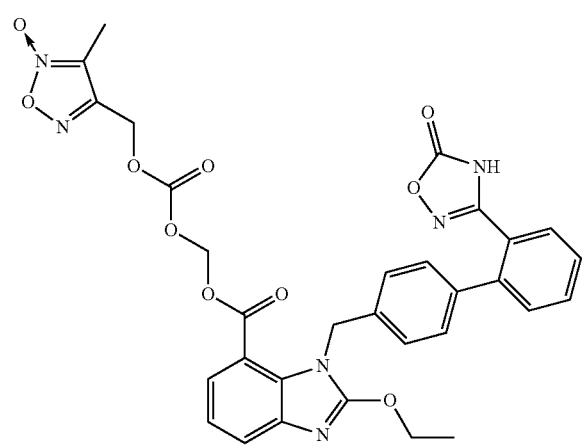
QR01023
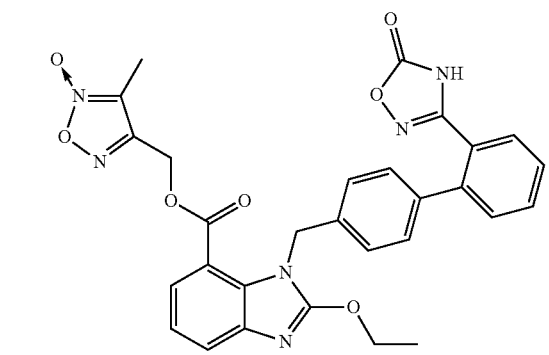
34
-continued
QR01026
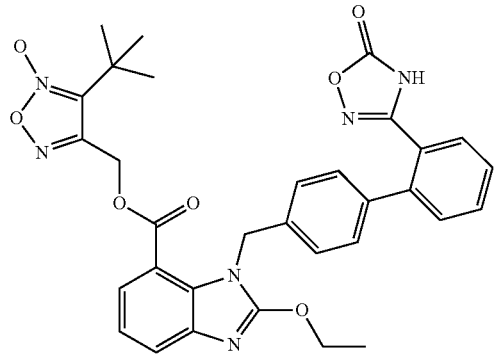
QR01030
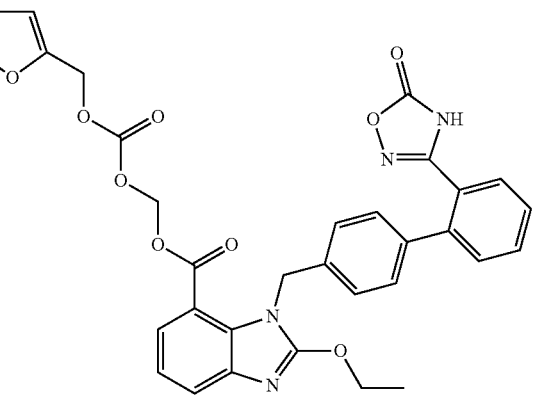
QR01031
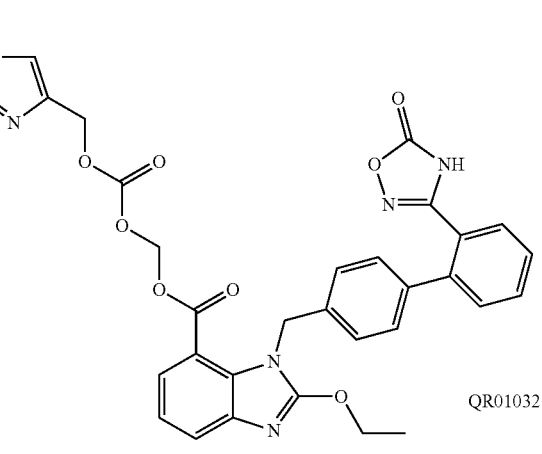
QR01032
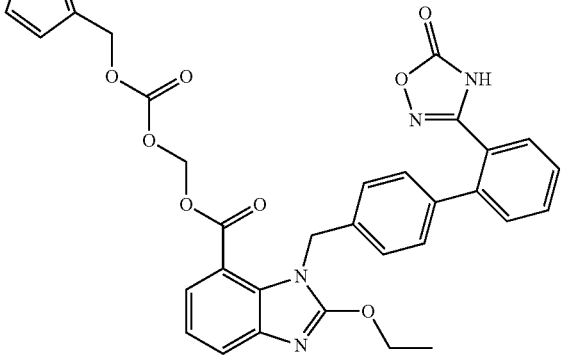

-continued
QR01033
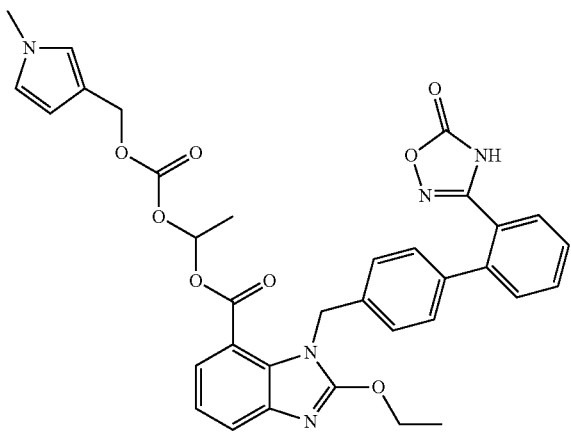
QR01034
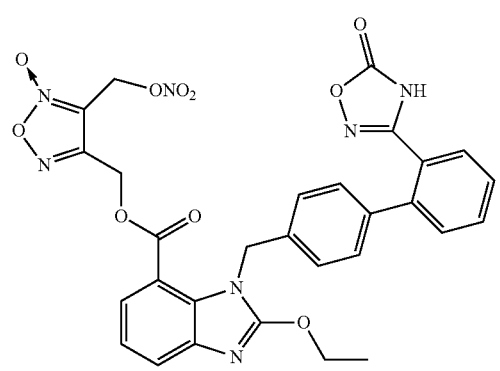
QR01035
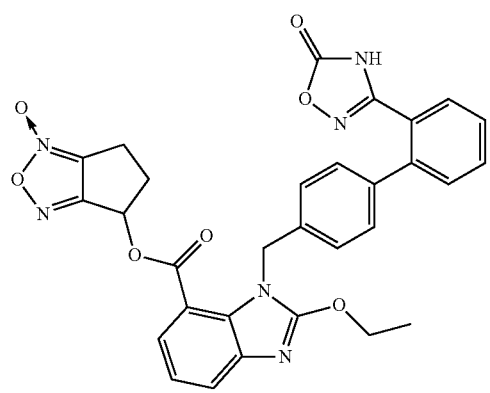
QR01036
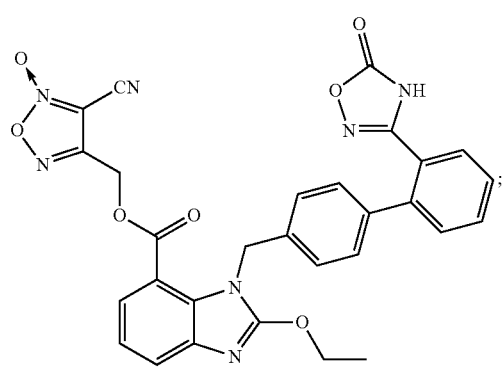
and the compound of formula (II) has one of structures shown below:
QR01005K
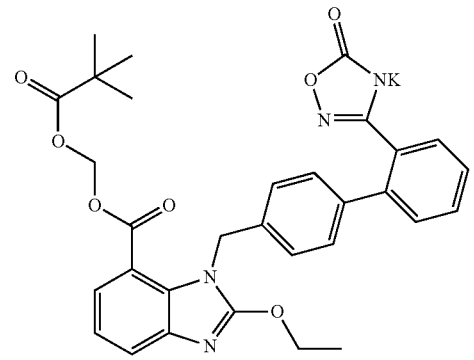
QR01008K
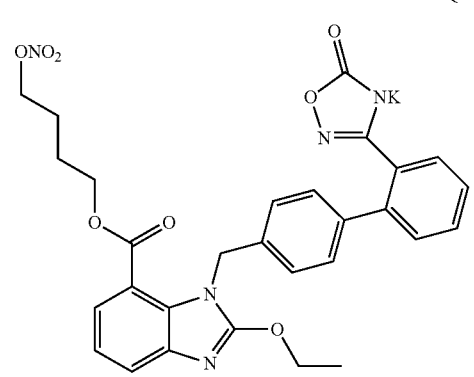
QR01009K
QR01011K
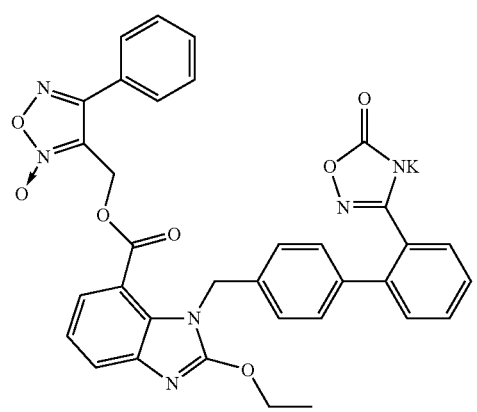

37
-continued
QR01013K
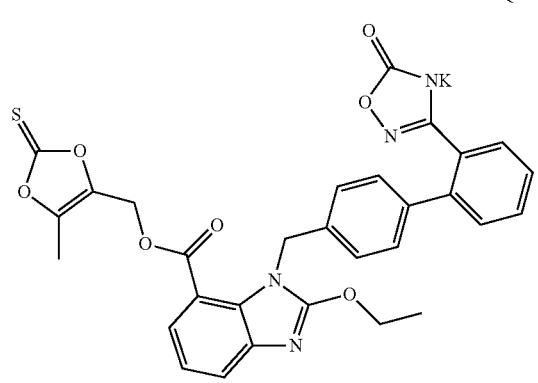
QR01017K
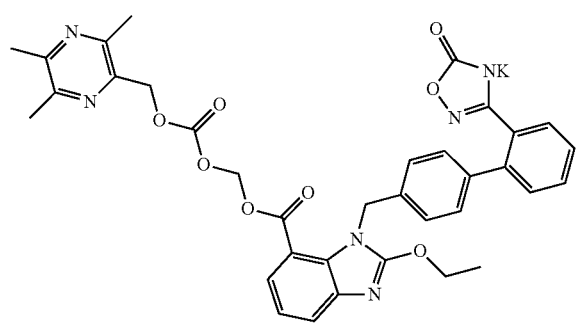
QR01019K
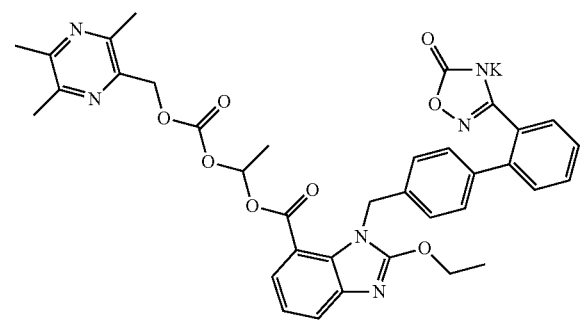
QR01020K
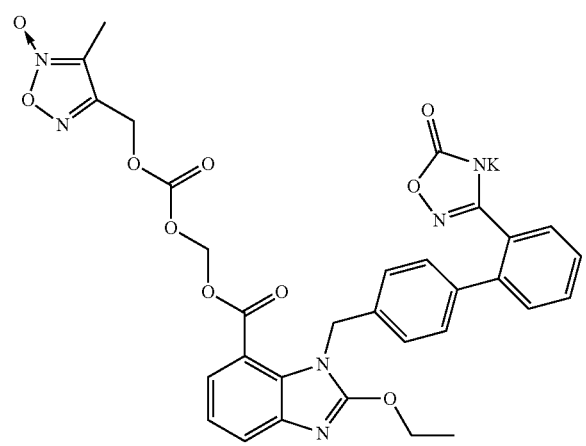
38
-continued
QR01023K
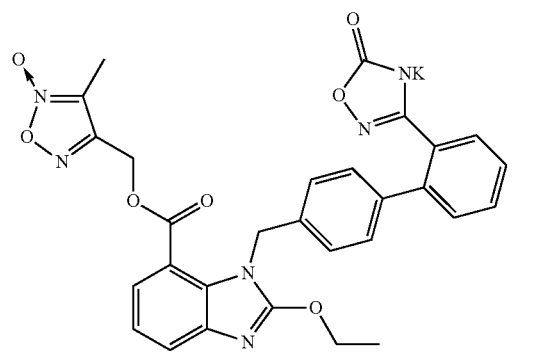
QR01026K
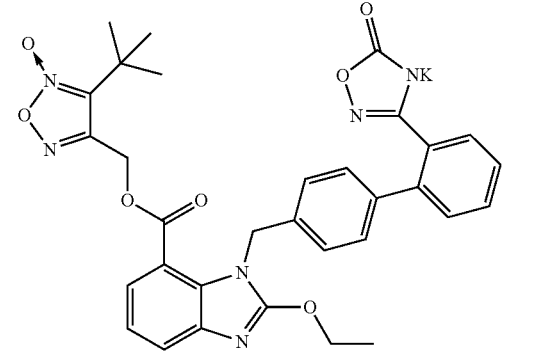
QR01030K
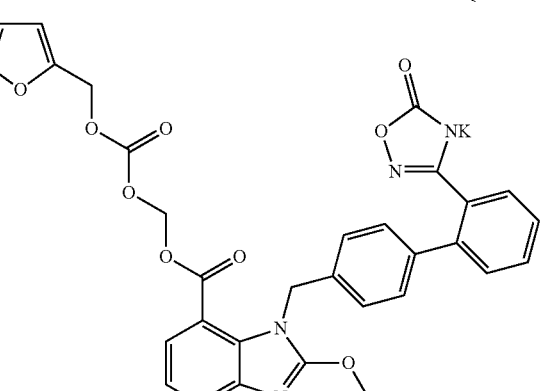
QR01031K
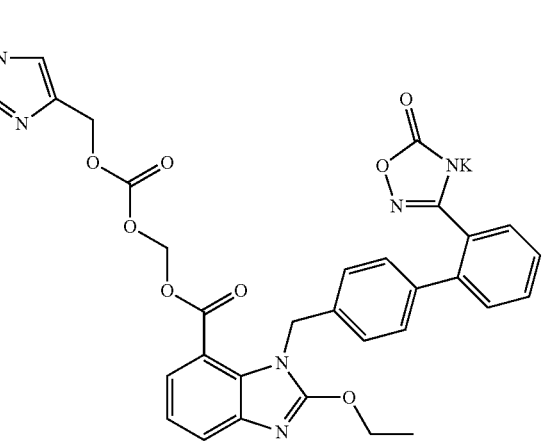

-continued

QR01032K

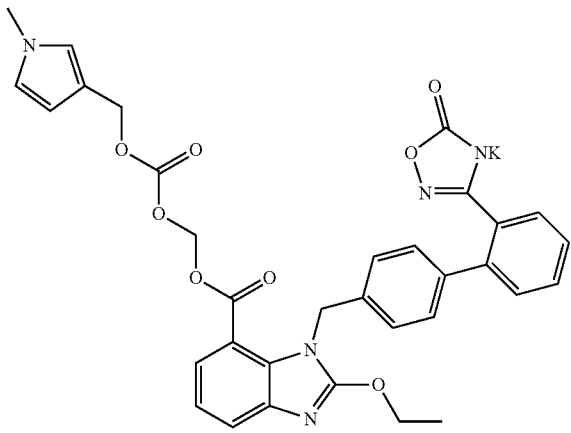

QR01033K

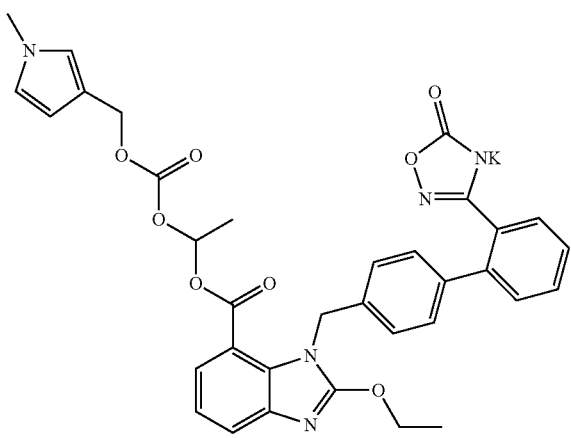

QR01034K

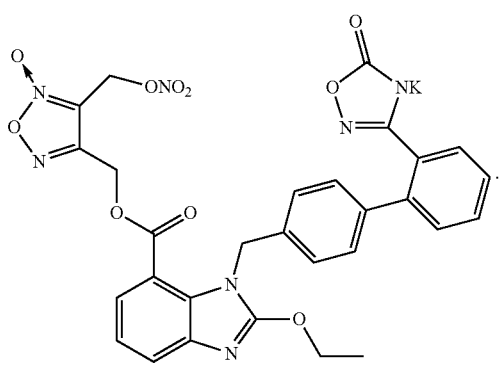

3. The oral solid preparation according to claim 1, wherein the excipient is selected from at least one of the group consisting of starch, lactose, mannitol, cellulose lactose, microcrystalline cellulose, calcium hydrogen phosphate and mannitol-starch complex; the lubricant is selected from at least one of the group consisting of talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

4. The oral solid preparation according to claim 1, further comprising a binder, wherein
the binder is selected from at least one of the group consisting of starch and derivatives thereof (including but not limited to starch, pregelatinized starch, dextrin and maltodextrin), cellulose derivatives (including but not limited to methylcellulose, carboxy methylcellulose sodium, hydroxypropylcellulose, hypromellose, ethylcellulose and microcrystalline cellulose), natural and synthetic rubbers (including but not limited to gelatin, gum arabic, locust gum, peach glue), polyethylene glycol, povidone, glycerol dibehenate, carbomer, polyvinyl alcohol, poly(meth)acrylic resin, sugar alcohols (including but not limited to sucrose, liquid glucose, maltose alcohol), corn gluten, sodium alginate, and monolaurate
and a content of the binder is about 0-15% by weight.

5. An oral solid preparation according to claim 1, wherein, the active ingredient is QR01019 or QR01019K as shown below:

QR01019

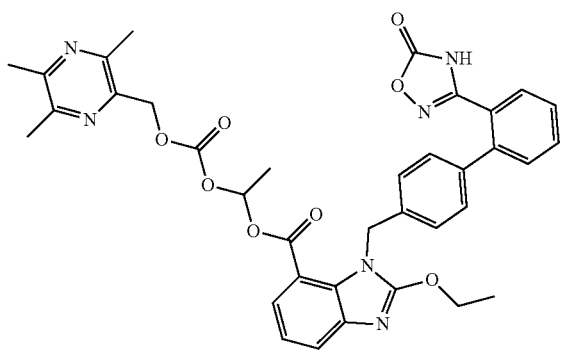

QR01019K

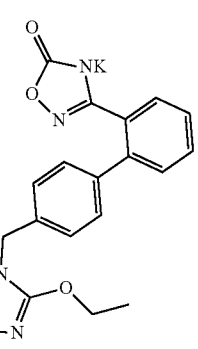

and the oral solid preparation is a tablet.

6. The oral solid preparation according to claim 5, wherein the excipient is selected from at least one of the group consisting of starch, lactose, mannitol, cellulose lactose, microcrystalline cellulose, calcium hydrogen phosphate and mannitol-starch complex; the lubricant is selected from at least one of the group consisting of talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

7. The oral solid preparation according to claim 5, further comprising a binder, wherein
the binder is selected from at least one of the group consisting of starch and derivatives thereof (including but not limited to starch, pregelatinized starch, dextrin and maltodextrin), cellulose derivatives (including but not limited to methylcellulose, carboxy methylcellulose sodium, hydroxypropylcellulose, hypromellose, ethylcellulose and microcrystalline cellulose), natural and synthetic rubbers (including but not limited to gelatin, gum arabic, locust gum and peach glue), polyethylene glycol, povidone, glycerol dibehenate, carbomer, polyvinyl alcohol, poly(meth)acrylic resin, sugar alcohols (including but not limited to sucrose, liquid glucose and maltose alcohol), corn gluten, sodium alginate, and monolaurate;

and a content of the binder is about 0-15% by weight.

8. A method of antagonizing an angiotensin II receptor or treating hypertension, chronic heart failure, or diabetic nephropathy, comprising administering an effective amount of the oral solid preparation according to claim 1 to a subject in need thereof.

9. The oral solid preparation according to claim 2, wherein the excipient is selected from at least one of the group consisting of starch, lactose, mannitol, cellulose lactose, microcrystalline cellulose, calcium hydrogen phosphate and mannitol-starch complex; the lubricant is selected from at least one of the group consisting of talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

10. The oral solid preparation according to claim 2, further comprising a binder, wherein, the binder is selected from at least one of the group consisting of starch and derivatives thereof (including but not limited to starch, pregelatinized starch, dextrin and maltodextrin), cellulose derivatives (including but not limited to methylcellulose, carboxy methylcellulose sodium, hydroxypropylcellulose, hypromellose, ethylcellulose and microcrystalline cellulose), natural and synthetic rubbers (including but not limited to gelatin, gum arabic, locust gum, peach glue), polyethylene glycol, povidone, glycerol dibehenate, carbomer, polyvinyl alcohol, poly(meth)acrylic resin, sugar alcohols (including but not limited to sucrose, liquid glucose, maltose alcohol), corn gluten, sodium alginate, and monolaurate;

and a content of the binder is about 0-15% by weight.

11. The oral solid preparation according to claim 3, further comprising a binder, wherein, the binder is selected from at least one of the group consisting of starch and derivatives thereof (including but not limited to starch, pregelatinized starch, dextrin and maltodextrin), cellulose derivatives (including but not limited to methylcellulose, carboxy methylcellulose sodium, hydroxypropylcellulose, hypromellose, ethylcellulose and microcrystalline cellulose), natural and synthetic rubbers (including but not limited to gelatin, gum arabic, locust gum, peach glue), polyethylene glycol, povidone, glycerol dibehenate, carbomer, polyvinyl alcohol, poly(meth)acrylic resin, sugar alcohols (including but not limited to sucrose, liquid glucose, maltose alcohol), corn gluten, sodium alginate, and monolaurate;

and a content of the binder is about 0-15% by weight.

12. The oral solid preparation according to claim 6, further comprising a binder, wherein the binder is selected from at least one of the group consisting of starch and derivatives thereof (including but not limited to starch, pregelatinized starch, dextrin and maltodextrin), cellulose derivatives (including but not limited to methylcellulose, carboxy methylcellulose sodium, hydroxypropylcellulose, hypromellose, ethylcellulose and microcrystalline cellulose), natural and synthetic rubbers (including but not limited to gelatin, gum arabic, locust gum and peach glue), polyethylene glycol, povidone, glycerol dibehenate, carbomer, polyvinyl alcohol, poly(meth)acrylic resin, sugar alcohols (including but not limited to sucrose, liquid glucose and maltose alcohol), corn gluten, sodium alginate, and monolaurate;

and a content of the binder is about 0-15% by weight.

13. A method of antagonizing an angiotensin II receptor or treating hypertension, chronic heart failure, or diabetic nephropathy, comprising administering an effective amount of the oral solid preparation according to claim 2 to a subject in need thereof.

* * * * *